United States Patent [19]

Horii et al.

[11] Patent Number: 4,777,294

[45] Date of Patent: Oct. 11, 1988

[54] N-SUBSTITUTED PSEUDO-AMINOSUGARS, THEIR PRODUCTION AND USE

[75] Inventors: Satoshi Horii, Sakai; Yukihiko Kameda, Kanazawa; Hiroshi Fukase, Osaka, all of Japan

[73] Assignee: Takeda Chemical Industries, Ltd., Osaka, Japan

[21] Appl. No.: 39,278

[22] Filed: Apr. 17, 1987

Related U.S. Application Data

[62] Division of Ser. No. 334,986, Dec. 28, 1981, Pat. No. 4,701,559.

[30] Foreign Application Priority Data

Jan. 5, 1981 [JP] Japan .................. 56-561
Jun. 2, 1981 [JP] Japan .................. 56-84635
Oct. 6, 1981 [JP] Japan .................. 56-159657

[51] Int. Cl.$^4$ .................................... C07C 91/16
[52] U.S. Cl. .................................... 564/363; 549/74; 549/452; 564/353; 564/355; 564/360; 564/364; 564/374; 564/376; 564/381; 564/382; 564/383; 564/384; 564/386; 564/389; 564/391; 564/392; 564/462
[58] Field of Search ............... 564/363, 353, 355, 360, 564/462, 1; 504/374; 546/348; 549/74, 452

[56] References Cited

U.S. PATENT DOCUMENTS 4,701,559 10/1987 Horii et al. ................... 564/363

Primary Examiner—Robert V. Hines
Attorney, Agent, or Firm—Wegner & Bretschneider

[57] ABSTRACT

A compound of the formula:

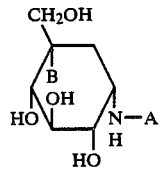

wherein A is a chain hydrocarbon group having 1 to 10 carbon atoms optionally substituted by hydroxyl, phenoxy, thienyl, furyl, pyridyl, cyclohexyl or an optionally substituted phenyl group, or a cyclic hydrocarbon group having 3 to 7 carbon atoms optionally substituted by hydroxyl, B is hydrogen or hydroxyl, and their production and use.

These compounds exhibit excellent inhibitory activity against α-glucoside hydrolase, thus are useful for hyperglycemic symptoms and various disorders caused by hyperglycemia.

6 Claims, No Drawings

N-SUBSTITUTED PSEUDO-AMINOSUGARS, THEIR PRODUCTION AND USE

This application is a division of Ser. No. 334,986, filed Dec. 28, 1981 and now U.S. Pat. No. 4,701,559.

The present invention relates to N-substituted Pseudo-aminosugars having an inhibitory activity against glucoside hydrolase, to processes for producing the same, and to α-glucosidase inhibitors containing the above-mentioned derivatives.

The present inventors previously isolated as a constituent of validamycin, an antibiotic, the compound of the formula

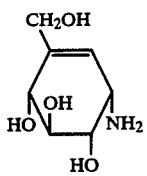

which was named "valienamine" (Y. Kameda and S. Horii; Journal of the Chemical Society; Chemical Communications, 1972, 746 to 747), and reported that valienamine possesses an action of suppressing the function of α-glucoside hydrolase (Y. Kameda et al., Journal of Antibiotics 33, 1575 to 1576 (1980)). In recent years, various compounds having valienamine moiety, which exhibit α-glycosidase inhibitory activity, are reported e.g. "Acarbose" in U.S. Pat. No. 4,062,950, "Trestatin A, B and C" in German laid open patent application No. 2,905,649 but their actions to suppress the function of α-glucoside hydrolase are unsatisfactory.

The present inventors investigated an α-glycosidase inhibitory activity of various compounds which are similar to valienamine in chemical structure and, after lots of research, found that validamine [Horii et al., Journal of Antibiotics 24, pp. 59 to 63 (1971)] possesses a highly valuable action of suppressing the function of a α-glucoside hydrolase or the action as an α-glucosidase inhibitor. The present inventors also found that valiolamine of the formula

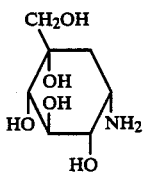

which was discovered and isolated from a culture broth of the genus streptomyces, possesses α-glucosidase inhibitory activity. These findings were further followed by continued studies on various novel derivatives of validamine and valiolamine, and as a result, it was found that a group of N-substituted derivatives of validamine and valiolamine exhibits stronger α-glucosidase inhibitory activity than valienamine, which has culminated in the present invention.

Thus, the present invention relates to a compound of the formula

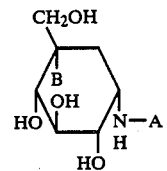

wherein A is a chain hydrocarbon group having 1 to 10 carbon atoms optionally substituted by hydroxyl, phenoxy, thienyl, furyl, pyridyl, cyclohexyl or an optionally substituted phenyl group, or a cyclic hydrocarbon group having 3 to 7 carbon atoms optionally substituted by hydroxyl; B is hydrogen or hydroxyl, processes for producing the compound [I] and an α-glucosidase inhibitor containing the compound [I].

Referring to the compounds [I], the chain hydrocarbon group of 1 to 10 carbon atoms represented by A includes straight-chain saturated, aliphatic hydrocarbon groups such as ($C_{1-10}$) alkyl e.g. methyl, ethyl, propyl, butyl, pentyl, hexyl, heptyl, octyl, nonyl and decyl; branched saturated, aliphatic hydrocarbon groups, such as lower ($C_{3-5}$) alkyl e.g. isopropyl, isobutyl, sec-butyl, tert-butyl, neopentyl and tert-pentyl, ($C_{4-9}$) alkyl having one or two methyls e.g. 1-methylbutyl, 2-methylbutyl, isohexyl, 1-methylpentyl, 2-methylpentyl, 3-methylpentyl, 4-methylpentyl, methylhexyl exemplified by 5-methylhexyl, etc., methylheptyl exemplified by 1-methylheptyl, etc., methyloctyl, methylnonyl, 1-methylisobutyl, 1-methylisopentyl, dimethylbutyl exemplified by 1,1-dimethybutyl, etc., dimethylpentyl exemplified by 1,1-dimethylpentyl, 1,4-dimethylpentyl, etc., dimethylhexyl, dimethylheptyl and dimethyloctyl, ($C_{3-8}$) alkyl having one or two ethyls e.g. 1-ethylpropyl, ethylbutyl, ethylpentyl, ethylhexyl, ethylheptyl and ethyloctyl, ($C_{3-4}$) alkyls having methyl and ethyl e.g. ethylmethylpropyl exemplified by 1-ethyl-1-methylpropyl, etc., ethylmethylbutyl exemplified by 1-ethyl-2-methylbutyl, 1-ethyl-3-methylbutyl, etc., and propylbutyl exemplified by 1-isopropylbutyl, etc.; and straight-chain and branched unsaturated aliphatic hydrocarbon groups such as propenyl exemplified by vinyl, allyl, etc., butenyl exemplified by 3-butenyl, etc., pentenyl exemplified by 4-pentenyl, etc., hexenyl, heptenyl, octenyl, nonenyl, decenyl, butadienyl, pentadienyl, hexadienyl, heptadienyl, octadienyl, nonadienyl, decadienyl, hexatrienyl, heptatrienyl, octatrienyl, nonatrienyl, decatrienyl, octatetraenyl, nonatetraenyl, decatetraenyl, decapentaenyl, isopropenyl, methylpropenyl exemplified by 2-methylallyl, etc., dimethylpropenyl exemplified by 1,1-dimethylallyl, etc., methylbutenyl exemplified by 3-methyl-2-butenyl, 3-methyl-3-butenyl, etc., and dimethyldienyl unsaturated hydrocarbon groups exemplified by 3,7-dimethyl-2,6-octadienyl, etc. As preferable ones among them, there may be mentioned chain hydrocarbons of 1 to 6 carbon atoms. These hydrocarbon groups may be substituted by one or more of hydroxyl, cyclohexyl, phenoxy, thienyl, furyl, pyridyl or a phenyl group which may be substituted with hydroxyl, a lower alkoxy such as methoxy, ethoxy, n-propoxy and isopropoxy carboxyl, a halogen such as fluorine, chlorine, bromine and iodine, phenyl or a lower alkyl such as methyl, ethyl, propyl, isopropyl, butyl, sec-butyl and tert-butyl. Preferably the above-mentioned substituents are hydroxyl or phenyl groups which may be substituted by hydroxy, lower alkoxy, lower alkyl or halogen. The cyclic hydrocarbon group of 3 to 7 carbon atoms represented by A includes cyclic saturated hydrocarbon groups such as cyclopropyl, cyclobutyl, cyclopentyl, cyclohexyl and cycloheptyl; cyclic unsaturated hydrocarbon groups such as cyclopropenyl, cyclobutenyl, cyclopentenyl, cyclohexenyl and cycloheptenyl. As preferable ones among them, there may be mentioned cyclic hydrocarbons of 5 to 6 carbon atoms. These cyclic hydrocarbon groups may be optionally substituted by one to six hydroxyl groups.

Furthermore, specific examples of the N-substituted pseudo-aminosugars represented by the formula [I] include:

(1) N-benzylvalidamine;
(2) N-phenetylvalidamine;
(3) N-(3-phenylpropyl)validamine;
(4) N-(4-phenylbutyl)validamine;
(5) N-(5-phenylpentyl)validamine;
(6) N-(6-phenylhexyl)validamine;
(7) N-(3-phenylallyl)validamine;
(8) N-furfurylvalidamine;
(9) N-thenylvalidamine;
(10) N-(3-pyridylmethyl)validamine;
(11) N-(4-methylbenzyl)validamine;
(12) N-(4-methoxybenzyl)validamine;
(13) N-(3-phenoxypropyl)validamine;
(14) N-(2-phenylpropyl)validamine;
(15) N-n-butylvalidamine;
(16) N-(4-bromobenzyl)validamine;
(17) N-(4-carboxybenzyl)validamine;
(18) N-($\beta$-hydroxyphenetyl)validamine;
(19) N-($\beta$-hydroxy-2-methoxyphenetyl)validamine;
(20) N-($\beta$-hydroxy-2-chlorophenetyl)validamine;
(21) N-($\alpha$-methylbenzyl)validamine;
(22) N-($\alpha$-methylphenetyl)validamine;
(23) N-(4-hydroxybenzyl)validamine;
(24) N-(3,4-dihydroxybenzyl)validamine;
(25) N-(3,5-di-tert-butyl-4-hydroxybenzyl)validamine;
(26) N-(2-diphenylethyl)validamine;
(27) N-(cyclohexylmethyl)validamine;
(28) N-geranylvalidamine;
(29) N-(1,3-dihydroxy-2-propyl)validamine;
(30) N-(1,3-dihydroxy-1-phenyl-2-propyl)validamine;
(31) N-[$\alpha$-(hydroxymethyl)benzyl]validamine;
(32) N-(D-gluco-2,3,4,5,6-pentahydroxyhexyl)validamine;
(33) N-(D-manno-2,3,4,5,6-pentahydroxyhexyl)validamine;
(34) N-(D-galacto-2,3,4,5,6-pentahydroxyhexyl)validamine;
(34) N-(D-arabo-2,3,4,5-tetrahydroxypentyl)validamine;
(36) N-(D-ribo-2,3,4,5-tetrahydroxypentyl)validamine;
(37) N-(D-xylo-2,3,4,5-tetrahydroxypentyl)validamine;
(38) N-(D-arabo-2,3,4,5-tetrahydroxy-1-hydroxymethylpentyl)validamine;
(39) N-(L-xylo-2,3,4,5-tetrahydroxy-1-hydroxymethylpentyl)validamine;
(40) N-(2-hydroxycyclohexyl)validamine;
(41) N-cyclohexylvalidamine;
(42) N-(2-hydroxycyclopentyl)validamine;
(43) N-cyclopentylvalidamine;
(44) N-[(1R,2R)-2-hydroxycyclohexyl]validamine;
(45) N-[(1S,2S)-2-hydroxycyclohexyl]validamine;
(46) N-[(1R,2R)-2-hydroxycyclopentyl]validamine;
(47) N-[(1S,2S)-2-hydroxycyclopentyl]validamine;
(48) N-benzylvaliolamine;
(49) N-phenetylvaliolamine;
(50) N-(3-phenylpropyl)valiolamine;
(51) N-(4-phenylbutyl)valiolamine;
(52) N-(5-phenylpentyl)valiolamine;
(53) N-(6-phenylhexyl)valiolamine;
(54) N-(3-phenylallyl)valiolamine;
(55) N-furfurylvaliolamine;
(56) N-thenylvaliolamine;
(57) N-(3-pyridylmethyl)valiolamine;
(58) N-(4-methylbenzyl)valiolamine;
(59) N-(4-methoxybenzyl)valiolamine;
(60) N-(3-phenoxypropyl)valiolamine;
(61) N-(2-phenylpropyl)valiolamine;
(62) N-n-butylvaliolamine;
(63) N-(4-bromobenzyl)valiolamine;
(64) N-(4-carboxybenzyl)valiolamine;
(65) N-($\beta$-hydroxyphenetyl)valiolamine;
(66) N-($\beta$-hydroxy-2-methoxyphenetyl)valiolamine;
(67) N-($\beta$-hydroxy-2-chlorophenetyl)valiolamine;
(68) N-($\alpha$-methylbenzyl)valiolamine;
(69) N-($\alpha$-methylphenetyl)valiolamine;
(70) N-(4-hydroxybenzyl)valiolamine;
(71) N-(3,4-dihydroxybenzyl)valiolamine;
(72) N-(3,5-di-tert-butyl-4-hydroxybenzyl)valiolamine;
(73) N-(2-diphenylethyl)valiolamine;
(74) N-(cyclohexylmethyl)valiolamine;
(75) N-geranylvaliolamine;
(76) N-(1,3-dihydroxy-2-propyl)valiolamine;
(77) N-(1,3-dihydroxy-1-phenyl-2-propyl)valiolamine;
(78) N-[$\alpha$-(hydroxymethyl)benzyl]valiolamine;
(79) N-(D-gluco-2,3,4,5,6-pentahydroxyhexyl)valiolamine;
(80) N-(D-manno-2,3,4,5,6-pentahydroxyhexyl)valiolamine;
(81) N-(D-galacto-2,3,4,5,6-pentahydroxyhexyl)valiolamine;
(82) N-(D-arabo-2,3,4,5-tetrahydroxypentyl)valiolamine;
(83) N-(D-ribo-2,3,4,5-tetrahydroxypentyl)valiolamine;
(84) N-(D-xylo-2,3,4,5-tetrahydroxypentyl)valiolamine;
(85) N-(D-arabo-2,3,4,5-tetrahydroxy-1-hydroxymethylpentyl)valiolamine;
(86) N-(L-xylo-2,3,4,5-tetrahydroxy-1-hydroxymethylpentyl)valiolamine;
(87) N-(2-hydroxycyclohexyl)valiolamine;
(88) N-cyclohexylvaliolamine;
(89) N-(2-hydroxycyclopentyl)valiolamine;
(90) N-cyclopentylvaliolamine;
(91) N-[(1R,2R)-2-hydroxycycohexyl]valiolamine;
(92) N-[(1S,2S)-2-hydroxycyclohexyl]valiolamine;
(93) N-[(1R,2R)-2-hydroxycyclopentyl]valiolamine;
(94) N-[(1S,2S)-2-hydroxycyclopentyl]valiolamine.

The $\alpha$-glucosidase inhibitor of the present invention, because of its ability to suppress the metabolism of carbohydrates in man and other animals, exhibits the blood-sugar elevation suppressing function, and is a compound useful for hyperglycemic symptoms and various disorders caused by hyperglycemia such as obesity, adiposity, hyperlipemia (arteriosclerosis), diabetes, and prediabetes as well as prophylaxis of diseases attributable to sugar metabolism by microorganisms in oral cavity such as dental caries. Foods prepared by adding compounds [I] are useful as a therapeutic diet for patients affected with metabolic abnormality and as a prophylactic diet for healthy persons, as well. In addition, the derivatives are of use as an additive for livestock feed which helps to obtain low-fat, high-quality animal flesh for food. Therefore, the $\alpha$-glucosidase inhibitors of the present invention are of value as drugs, food additives and livestock feed additives. The $\alpha$- glucosidase inhibitors of the present invention are administered orally or parenterally, preferably orally.

The above-mentioned compounds [I] are stable crystals or powders and almost free from toxicity ($LD_{50}$ in rats, not lower than 1000 mg), and can be utilized as a free base or hydrate and also as any non-toxic acid addition salts formed with pharmacologically allowable acids by conventional methods. As examples of such acids, use is made of inorganic acids such as hydrochloric acid, hydrobromic acid, sulfuric acid, phosphoric acid and nitric acid, and organic acids such as acetic acid, malic acid, citric acid, ascorbic acid, mandelic acid and methanesulfonic acid. Such compounds [I] are used solely or as mixtures with non-toxic carriers, and may be utilized with liquid or solid foods such as coffee, beverages, fruit juice, beer, milk, jam, bean jam and jelly, seasoning agents, or the principal and subsidiary foods, etc. They can be used directly or in the form of a food additives, or can be administered before or after meals. Further, they can also find application as additives for likestock feed which serve to obtain low-fat, high-quality animal flesh for food.

The inhibitors of the present invention can be diluted with non-toxic carriers, for example, such liquid carries as water, ethanol, ethylene glycol and polyethylene glycol, and such solid carriers as starch, cellulose and polyamide powders, and prepared into ampoules, granules, tablets, pills, capsules, syrups, etc. by conventional methods to utilize in the above-mentioned, various application fields. In addition, they can also be used in combination with sweetening, preservatives, dispersing agents and coloring agents.

Specifically, preparations containing for example 20 to 300 mg of the compound [I], when given after each meal, can suppress elevation of postprandial blood glucose lebel. Furthermore, the compounds [I] may be added to various foods at ratios in the range of 0.01 to 1% of a carbohydrate content in the food.

In the case of blending in livestock feed, it is desirable to add in the ratio of 0.001 to 1% of a carbohydrate content in feed.

The compounds [I] of the present invention are all the novel compounds that have not been described in the literature, and can be synthesized for example by the following method: that is to say, they can be synthesized by subjecting to a reduction reaction a Schiff's base obtained by reacting a chain aldehyde or ketone of 1 to 10 carbon atoms optionally substituted by hydroxyl, phenoxy, thienyl, furyl, pyridyl, cyclohexyl or an optionally substituted phenyl group; or a cyclic ketone having 3 to 7 carbon atoms optionally substituted by hydroxyl and validamine or valiolamine in an appropriate solvent. The condensation reaction of an amino group in validamine or valiolamine with aldehyde or ketone, and the subsequent reduction reaction may be consecutively conducted in the same reaction vessel, or the reactions may be carried out separately in two stages. As the reaction solvent, use can be made of polar solvents such as water, alcohols e.g. methanol, propanol and butanol, dimethylsulfoxide, dimethylformamide, N-methylacetamide, glymes e.g. methyl cellosolve, dimethyl cellosolve and diethylene glycol dimethyl ether, dioxane, tetrahydrofuran and acetonitrile, or their mixed solvents, or mixtures of these polar solvents with non-polar solvents such as chloroform and dichloromethane.

The reaction temperature in the Schiff's base formation reaction is not particularly limited, and the reaction is carried out by heating at temperature in the range of room temperature to 100° C. The reaction times varies depending upon the reaction temperature and the type of aldehydes or ketones used, but the desired objective can be achieved normally by allowing the reaction to proceed for a period in the range of several minutes to 24 hours.

For the purpose of the reduction reaction of the Schiff's base formed, use is advantageously made of various reducing agents, for example, metal hydride complexes such as alkali-metal borohydrides, e.g., sodium borohydride, potassium borohydride, lithium borohydride and sodium trimethoxy borohydride, alkali-metal cyanoborohydrides, e.g., sodium cyanoborohydride, alkali-metal aluminium hydrides, e.g., lithium aluminium hydride, and dialkylamine boranes, e.g., dimethylamine borane. In cases in which alkali-metal cyanohydrides such as sodium cyanohydride are used, further, it is desirable to conduct the reaction under acid conditions, for example, in the presence of hydrochloric acid, acetic acid, etc.

The reaction temperature is not particularly limited, and the reaction is conducted normally at room temperature or, as the case may be, by heating at temperature up to about 100° C.; the reaction temperature varies depending upon the type of Schiff's bases and the kind of reducing agents. The reaction time also varies according to the reaction temperature and the kinds of Schiff's bases to be reduced and reducing agents, and the desired objective can be attained normally by allowing the reaction to proceed for a period in the range of several minutes to 24 hours.

For the purpose of a reduction reaction of the Schiff's base formed, use is also made of means of catalytic reduction. That is to say, the reduction reaction is conducted by shaking or stirring a Schiff's base in an appropriate solvent in the presence of a catalyst for catalytic reduction under a stream of hydrogen. As the catalyst for catalytic reduction, use is for example made of platinum black, platinum dioxide, palladium black, palladium carbon, Raney nickel, etc., while, as the solvent which is normally utilized, use is for example made of water, alcohols such as methanol and ethanol, dioxane, tetrahydrofurane, dimethylformamide or mixed solvents consisting of these. The reaction is normally conducted at room temperature, and may be carried out either under pressure or by heating.

The compound [I] can be synthesized by reacting with validamine or valiolamine in an appropriate solvent a chain hydrocarbon halide of 1 to 10 carbon atoms optionally substituted by hydroxyl, phenoxy, thienyl, furyl, pyridyl, cyclohexyl or an optionally substituted phenyl group, or a cyclic hydrocarbon halide have 3 to 7 carbon atoms optionally substituted by hydroxy.

As the appropriate reaction solvent, use is made of polar solvents such as water, lower alkanols e.g. methanol, ethanol, propanol and butanol, ketones e.g. acetone, methyl ethyl ketone and methyl isobutyl ketone, dimethylsulfoxide, dimethylformamide, N-methylacetamide, glymes e.g. methyl cellosolve, ethylene glycol dimethyl ether and diethylene glycol dimethyl ether, dioxane, tetrahydrofuran and acetonitrile, or their mixed solvents, or mixed solvents of these with non-polar solvents such as benzene, hexane, chloroform, dichloromethane and ethyl acetate, and others. In cases in which such mixed solvent do not present the homogeneous phase, the reaction may be conducted in the presence of a phase-transfer catalyst such as tert-ammonium salt (e.g. tetrabutyl ammonium bromide), crown ether (e.g. dibenzo-18-crown-6) and phosphonium salt (e.g. hexadecyltri-n-butylphosphonium bromide).

In this reaction use can be made of inorganic and organic bases such as alkali-metal bicarbonates, alkali-metal carbonates, alkali-metal hydroxides, trimethylamine, triethylamine, tributylamine, N-methylmorpholine, N-methylpiperidine, N,N-dimethylaniline, pyridine, picoline and lutidine.

The reaction temperature is not particularly limited, and the reaction is conducted normally at room temperature or by heating at temperature up to about 100° C. The reaction time varies depending upon the reaction temperature, and the desired objective can be achieved normally by allowing the reaction to proceed for a period in the range of several minutes to 24 hours.

The compound [I] can be synthesized by the reaction of validamine or valiolamine with a compound of the formula

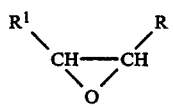

wherein $R^1$ is hydrogen; R is hydrogen, hydroxyl, phenoxy, thienyl, furyl, pyridyl, cyclohexyl or an optionally substituted phenyl; or a chain hydrocarbon group having 1 to 8 carbon atoms optionally substituted by hydroxyl, phenoxy, thienyl, furyl, pyridyl, cyclohexyl or an optionally substituted phenyl group, or $R^1$ and R may form together with the adjacent methine group a cyclic hydrocarbon group of 3 to 7 carbon atoms optionally substituted by hydroxyl; in an appropriate solvent. Referring to the compound [II], the examples of the substituents in an optionally substituted phenyl represented by R include hydroxyl, a lower alkoxy such as methoxy, ethoxy, n-propoxy and isopropoxy, carboxyl, a halogen such as fluorine, chlorine, bromine and iodine, phenyl or a lower alkyl such as methyl, ethyl, propyl, isopropyl, n-butyl, sec-butyl and tert-butyl. As examples of a cyclic hydrocarbon group of 3 to 7 carbon atoms, there may be mentioned the same ones as those of the cyclic hydrocarbon group of 3 to 7 carbon atoms represented by A.

As the appropriate reaction solvent, use is made of polar solvents such as water, lower alkanols e.g. methanol, ethanol, propanol and butanol, ketones e.g. acetone, methyl ethyl ketone and methyl isobutyl ketone, dimethylsulfoxide, dimethylformamide, N-methylacetamide, glymes e.g. methyl cellosolve, ethylene glycol dimethyl ether and diethylene glycol dimethyl ether, dioxane, tetrahydrofuran and acetonitrile, or their mixed solvents, or mixed solvents of these with nonpolar solvents such as benzene, hexane, chloroform, dichloromethane and ethyl acetate, and others. In cases in which such mixed solvents do not present the homogeneous phase, the reaction may be conducted in the presence of a phase-transfer catalyst such as crown ether, phosphonium salt and tert-ammonium salt.

The reaction temperature is not particularly limited, and the reaction is conducted normally at room temperature or by heating at temperature up to about 100° C. The reaction time varies depending upon the reaction temperature, and the desired object can be achieved normally by allowing the reaction to proceed for a period in the range of several minutes to 24 hours.

Thus obtained object compound [I] can be purified by per se conventional process, e.g. extraction, precipitation, crystallization, recrystallization, column chromatohraphy or thin-layer chromatography. Validamine as a starting material in this invention can be obtained by the method described in "Journal of Antibiotics; 24, 59 (1971)" and valiolamine employed as a starting material can be prepared from valienamine by the reaction schema as below.

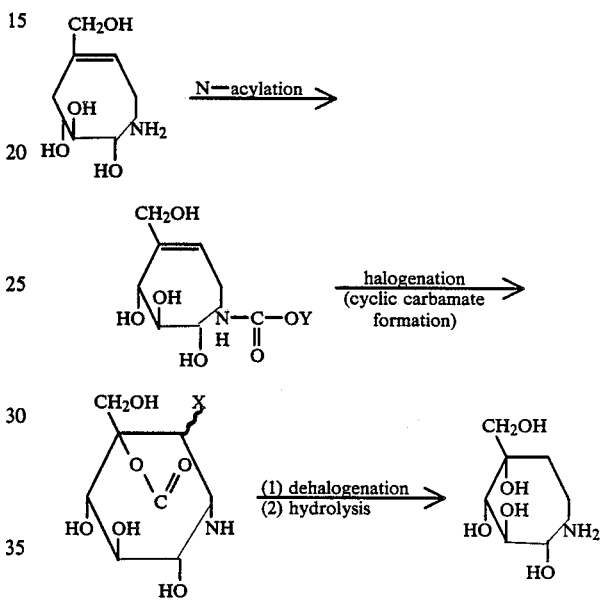

(In the formula, Y is an alkyl, an aryl or an aralkyl; X is a halogen)

Below described are the test example, the reference example and examples to illustrate in detail the contents of the present invention.

In the following Reference Examples and Examples, the eluate in column chromatography was monitored by thinlayer chromatography (TLC) with pre-coated silica gel plate (Kieselgel 60 $F_{254}$, Merck, W. Germany). The TLC was developed with n-propyl alcohol-acetic acid-water (4:1:1), and detection was effected by UV irradiation or with iodine vapor, unless otherwise specified. Rf-values of valienamine, validamine and valiolamine which were measured as reference standards by the method as mentioned above were as follows:

Valienamine: Rf=0.42
Validamine: Rf=0.35
Valiolamine: Rf=0.30

TEST EXAMPLE

The method of assaying the glucosidase inhibitory activity

The inhibitory activities of the compounds of this invention against α-glucosidase (yeast, type I, produced by Sigma Chemical Co. the United States of America) as well as maltase and saccharase prepared from porcine intestinal mucosa (prepared in accordance with the procedure as described by B. Borgström and A. Dahlgvist in Acta Chem. Scand.; 12, 1997-2006, (1958)), when maltose and sucrose are used at a substrate, are determined by adding to 0.25 ml of a solution of an enzyme prepared by diluting suitably with 0.02M phosphate buffer (pH 6.8) 0.5 ml of a solution of an inhibitory substance to be tested in the same buffer and 0.25 ml of 0.05M maltose or 0.05M sucrose as the substrate in the same buffer, allowing the mixture to react at 37° C. for 10 minutes, then adding 3 ml of Glucose B-Test Reagent (a glucose oxidase reagent for measurement of glucose, produced by Wako Pure Chemical Co., Japan), further warming the mixture at 37° C. for 20 minutes, and measuring the absorbance of the reaction solution at 505 nm.

The inhibitory activities against α-glucosidase (yeast, type I, produced by Sigma Chemical Co.) and glucoamylase (Rhizopus mold, produced by Sigma Chemical Co.), when p-nitrophenyl-α-D-glucopyranosidase is used as a substrate, are determined by adding to 0.25 ml of 0.02M phosphate buffer (pH 6.8) containing 0.005 mg/ml of α-glucosidase 0.5 ml of a solution of an inhibitor in the same buffer and 0.25 ml of a solution of 0.01M p-nitrophenyl-α-D-glucopyranosidase in the same buffer, allowing the reaction to proceed at 37° C. for 15 minutes, then adding 3 ml of 0.1M aqueous sodium carbonate solution to terminate the reaction, and measuring the absorbance of the reaction solution at 400 nm. The 50% inhibition concentration is calculated from the inhibition rates (%) which are determined with inhibitory substance samples of three to five different concentrations.

Table 1 shows the concentrations of 50% inhibition against maltase (from porcine intestinal mucosa) ($IC_{50}$) of compound [I] and Table 2 shows the concentrations of 50% inhibition against saccharase (from porcine intestinal mucosa) ($IC_{50}$) of compound [I].

TABLE 1

The concentrations of 50% inhibition against maltase (substrate: maltose) of compound [I] ($IC_{50}$)

| A | B | $IC_{50}$ (M) | A | B | $IC_{50}$ (M) |
|---|---|---|---|---|---|
| $-CH(CH_2OH)_2$ | OH | $1.5 \times 10^{-8}$ | $-CH_2CH(OH)CH_2O-\text{phenyl}$ | OH | $3.3 \times 10^{-8}$ |
| $-CH_2CH(OH)-\text{phenyl}$ ($[\alpha]_D +17°$) | OH | $5.0 \times 10^{-8}$ | $-CH_2CH_2-\text{phenyl}$ | OH | $1.0 \times 10^{-7}$ |
| $-CH_2-CH(OH)-\text{phenyl}$ ($[\alpha]_D -11°$) | OH | $5.8 \times 10^{-9}$ | $-(CH_2)_3-\text{phenyl}$ (HCl salt) | H | $9.2 \times 10^{-5}$ |
| $-CH_2-CH(OH)-\text{phenyl}$ (HCl salt) | H | $1.7 \times 10^{-6}$ | $-CH(CH_2OH)_2$ | H | $5.5 \times 10^{-7}$ |
| $-CH(CH_2OH)-CH(OH)-\text{phenyl}$ (HCl salt) | H | $3.2 \times 10^{-5}$ | $-CH_2-\text{phenyl}-OH$ (dimethyl) | H | $3.6 \times 10^{-5}$ |
| Valienamine (control) | | $1.7 \times 10^{-4}$ | | | |

TABLE 2

The concentrations of 50% inhibition against saccharase (substrate: sucrose) of compounds [I] ($IC_{50}$)

| A | B | $IC_{50}$ (M) | A | B | $IC_{50}$ (M) |
|---|---|---|---|---|---|
| $-CH(CH_2OH)_2$ | OH | $4.6 \times 10^{-9}$ | $-CH_2CH_2-\text{phenyl}$ | OH | $2.3 \times 10^{-9}$ |
| $-CH_2-CH(OH)-\text{phenyl}$ ($[\alpha]_D +17°$) | OH | $1.9 \times 10^{-8}$ | $-CH_2CH=CH-\text{phenyl}$ | OH | $1.4 \times 10^{-8}$ |

TABLE 2-continued

The concentrations of 50% inhibition against saccharase (substrate: sucrose) of compounds [I] (IC$_{50}$)

| A | B | IC$_{50}$ (M) | A | B | IC$_{50}$ (M) |
|---|---|---|---|---|---|
| 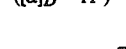 −CH$_2$−CH(OH)−C$_6$H$_5$ ([α]$_D$ −11°) | OH | 2.9 × 10$^{-9}$ |  −CH$_2$−C$_6$H$_4$−Br | OH | 1.5 × 10$^{-8}$ |
|  −CH$_2$CH(OH)CH$_2$O−C$_6$H$_5$ | OH | 8.6 × 10$^{-9}$ |  −CH$_2$-thienyl | | 3.3 × 10$^{-9}$ |
| 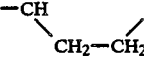 −CH$_2$−cyclohexyl | OH | 9.3 × 10$^{-9}$ | 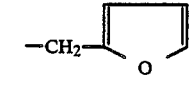 −CH$_2$-furyl | OH | 1.5 × 10$^{-8}$ |
| 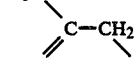 −CH$_2$−CH(C(CH$_3$)=CH$_2$)−CH$_2$−C(CH$_3$)=CH− (terpenoid) | OH | 1.1 × 10$^{-8}$ | 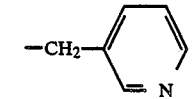 −CH$_2$-pyridyl | OH | 1.5 × 10$^{-8}$ |
| 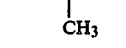 −CH$_2$−C(OH)H−C(OH)H−C(OH)H−C(OH)H−CH$_2$OH | OH | 3.6 × 10$^{-8}$ |  −CH$_2$−CH(OH)−C$_6$H$_5$ (HCl salt) | H | 2.2 × 10$^{-8}$ |
| 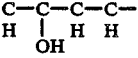 −(CH$_2$)$_3$−C$_6$H$_5$ (HCl salt) | H | 1.9 × 10$^{-6}$ | 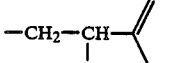 −CH(CH$_2$OH)−CH(OH)−C$_6$H$_5$ (HCl salt) | H | 2.6 × 10$^{-7}$ |
|  −CH(CH$_2$OH)$_2$ | H | 1.3 × 10$^{-8}$ | Valienamine (control) | | 5.3 × 10$^{-5}$ |

REFERENCE EXAMPLE

Valiolamine
(1L(1S)-(1(OH),2,4,5/1,3)-5-amino-1-hydroxymethyl-1,2,3,4-cyclohexanetetrol)

(1) Production of N-benzyloxycarbonylvalienamine

To a solution of 15 g of valienamine in 300 ml of water is added 100 ml of ethyl acetate, and then 25 ml of benzyloxycarbonylchrolide and 12 g of sodium hydrogen carbonate are added to the mixture at the same time under ice-cooling, followed by stirring for 3 hours at the room temperature. After the reaction mixture is adjusted to pH 6, the water layer is separated and washed with ethyl acetate. The obtained aqueous solution is concentrated to ca. 150 ml under reduced pressure. The concentrate is left standing overnight in a refrigerator to give 16.4 g of N-benzyloxycarbonylvalienamine as crystals.

(2) Production of 9-Bromo-6,7,8-trihydroxy-1-hydroxymethyl-3-oxo-2-oxa-4-azabicyclo[3,3,1]nonane To 100 ml of water which is cooled at 5°–10° C. are added dropwise a solution of 9.3 g of N-benzyloxycarbonylvalienamine in 200 ml of water and a solution of 5.3 g of bromine in 250 ml of water for 1 hr at the same time, keeping the temperature of reaction mixture at 5°–10° C. The reaction mixture is stirred for further 1.5 hours at the same temperature. The mixture is adjusted to pH 6 with a saturated solution of sodium hydrogen carbonate, and washed with ethyl acetate.

The water layer is separated and concentrated under reduced pressure. The residue is subjected to column-chromatography (MCI gel CHP-20P (600 ml), Mitsubishi Chemical Industries Ltd. Japan) by the use of water as an eluent. The eluate containing the desired product is collected, and concentrated to ca. 50 ml. The concentrate is left standing in a refrigerator to give 6.5 g of 9-bromo-6,7,8-trihydroxy-1-hydroxymethyl-3-oxo-2-oxa-4-azabicyclo[3,3,1]nonane as cristals.

Elementary analysis, for $C_8H_{12}NO_6Br \cdot H_2O$: Calcd.: C, 30.39; H, 4.46; N, 4.43; Br, 25.28; Found: C, 30.30; H, 4.54; N, 4.40; Br, 25.41.

$[\alpha]_D^{24} +41.5°$ (c=1, $H_2O$).

IR $\nu_{max}^{KBr}$ cm$^{-1}$: 1700(—CO—).

(3) Production of 6,7,8-trihydroxy-1-hydroxymethyl-3-oxo-2-oxa-4-azabicyclo[3,3,1]nonane To a solution of 1.0 g of 9-bromo-6,7,8-trihydroxy-1-hydroxymethyl-3-oxo-2-oxa-4-azalicyclo[3,3,1]nonane in 50 ml of water is added a solution of 0.5 g of sodium borohydride in 20 ml of water at room temperature, followed by stirring for another 2 hours. The reaction mixture is adjusted to pH 5 by adding acetic acid, followed by concentration under reduced pressure.

The residue is subjected to column chromatography (activated carbon, 180 ml). The column is washed with water, and eluted with 50% aqueous methanol. The eluate containing the desired product is collected and concentrated under reduced pressure. To the residue is added a mixture of methanol:ethanol (1:10), followed by standing in a refrigerator to give 560 mg of 6,7,8-trihydroxy-1-hydroxymethyl-3-oxo-2-oxa-4-azabicyclo[3,3,2]nonane as crystals.

Elemental analysis, for $C_8H_{13}NO_6$: Calcd.: C, 43.83; H, 5.98; N, 6.39; Found: C, 43.81; H, 5.95; N, 6.55.

$[\alpha]_D^{24} +36.4°$ (c=1, $H_2O$).

IR $\nu_{max}^{KBr}$ cm$^{-1}$: 1670(C=O).

NMR($D_2O$)TMS(External standard) δ: 2.07(1H, dd, J=2 and 15 Hz), 2.34(1H, dd, J=5 and 15Hz), 3.45–4.1(6H) mp. 254°–255° C. (dec.).

(4) Production of 1L(1S)-(1(OH),2,4,5/1,3)-5-amino-1-hydroxymethyl-1,2,3,4-cyclohexanetetrol To a solution of 4.0 g of 6,7,8-trihydroxy-1-hydroxymethyl-3-oxo-2-oxa-4-azabicyclo[3,3,1]nonane in 200 ml of water is added 16 g of barium hydroxide, followed by stirring under reflux for 4 hours at 70°–80° C.

The reaction mixture is cooled to room temperature. Carbondioxide is introduced into the mixture for 30 minutes and the precipitating barium carbonate is filtered off. The filtrate is concentrated under reduced pressure and the concentrate is subjected to column chromatography (250 ml of Amberlite CG-50,$NH_4^+$ type, Rohm & Haas Co., U.S.A.) The column is washed with water, and eluted with 0.1N aqueous ammonia. The fractions containing the desired product are collected, followed by concentration under reduced pressure. The residue is purified on a column-chromatography (1.1 l of Dowex 1×2, OH$^-$ type, Dow Chemical Co, U.S.A.) by the use of water as an eluent. Thus-purified fraction is concentrated under reduced pressure and lyophilized to give 3.3 g of 1L(1S)-(1(OH),2,4,5/1,3)-5-amino--hydroxymethyl-1,2,3,4-cyclohexanetetrol as white powder.

Elemental analysis, for $C_7H_{15}NO_5 \cdot H_2O$: Calcd.: C, 39.80; H, 8.11; N, 6.63; Found: C, 39.94; H, 8.08; N, 6.67.

$[\alpha]_D^{25} +19.6°$ (c=1, $H_2O$).

NMR($D_2O$)TMS(external standard) δ: 1.80(1H, dd, J=3.8 and 15.5), 2.07(1H, dd, J=3 and 15.5), 3.4–3.6(1H), 3.55 (1H, d, J=10), 3.63(2H), 3.72(1H, dd, J=4.2 and 10), 3.99(1H, t, j=10).

EXAMPLE 1

N-(1,3-dihydroxy-2-propyl)validamine

In 50 ml of dimethylsulfoxide is dissolved 2.0 g of validamine, and 3.4 g of dihydroxyacetone, 1.5 m of 2N hydrochloric acid and 2.6 g of sodium cyanoborohydride are added to the solution, followed by stirring at 60° to 65° C. for 16 hours. After the conclusion of the reaction, as much dimethylsulfoxide as possible is distilled off under reduced pressure, and the residue is dissolved in 100 ml of water. The solution is added for adsorption to a column (180 ml) of Amberlite CG-50 (H$^+$ type) (produced by Rohm & Haas Co. USA), and after the column is washed with water, the elution is conducted with 0.5N aqueous ammonia. The eluate is concentrated under reduced pressure, and the concentrate is further chromatographed on a column (250 ml) of Dowex 1×2 (OH$^-$ type) (produced by Dow Chemical Co.), followed by the elution with water. The eluate is concentrated under reduced pressure, and lyophilized to give 0.5 g of white powder of N-(1,3-dihydroxy-2-propyl)validamine.

Elemental analysis, for $C_{10}H_{21}NO_6$: Calcd. (%): C, 47.80; H, 8.42; N, 5.57; Found (%): C, 47.56; H, 8.81; N, 5.75.

$[\alpha]_D^{25} +74.0°$ (c=1, $H_2O$).

TLC: Rf=0.35.

EXAMPLE 2

N-(1,3-dihydroxy-2-propyl)validamine hydrochloride

In 150 ml of dimethylsulfoxide are dissolved 6.0 g of validamine and 10.0 g of dihydroxyacetone, and 4.5 ml of 2N hydrochloric acid and then 7.8 g of sodium cyanoborohydride are added to the solution, followed by stirring at 60° to 65° C. for 20 hours. The reaction solution is concentrated under reduced pressure, and the concentrate is then dissolved in 300 ml of water. The solution is made acid (not higher than pH 1) with 2N hydrochloric acid, stirred, adjusted to pH 4 with 1N sodium hydroxide and added to a column (250 ml) of Dowex 50W×8 (H$^+$ type) (produced by Dow Chemical Co.). After the column is washed with water, the elution is conducted with 0.5N aqueous ammonia, and the eluate is concentrated under reduced pressure. The concentrate is chromatographed on a column of Dowex 1×2 (OH$^-$ type, 750 ml) followed by the elution with water. The eluate is concentrated under reduced pressure, and the concentrate is adjusted to pH 3 with 2N hydrochloric acid and chromatographed on activated carbon (170 ml), followed by the elution with water. The eluate is concentrated under reduced pressure and lyophilized to give white powder of N-(1,3-dihydroxy-2-propyl)validamine hydrochloride. Yield of 3.5 g.

Elemental analysis, for $C_{10}H_{21}NO_6 \cdot HCl \cdot \frac{1}{2}H_2O$: Calcd. (%): C, 40.47; H, 7.81; N, 4.72; Cl, 11.95; Found (%): C, 40.30; H, 7.74; N, 4.58; Cl, 12.23.

$[\alpha]_D^{25} +49.3°$ (c=1, $H_2O$).

EXAMPLE 3

N-(1,3-dihydroxy-1-phenyl-2-propyl)validamine hydrochloride 2.0 g of validamine is dissolved in 30 ml of methanol under warming in a hot water bath, and 4.6 g of 2-bromo-1-phenyl-1,3-propanediol and 2.4 g of sodium hydrogen-carbonate are added to the solution, followed by stirring at 60° to 70° C. for 3 days. The reaction solution is filtered, and the filtrate is concentrated under reduced pressure. Water is added to the residue, and the solution is adjusted to pH 2.5 with 2N hydrochloric acid and washed with ethyl acetate. The water layer is concentrated under reduced pressure, and the concentrate is chromatographed on a column (450 ml) of MCI Gel CHP20P (produced by Mitsubishi Chemical Ind., Ltd.), followed by the elution with water. The eluate is concentrated under reduced pressure and lyophilized to give 1.4 g of white powder of N-(1,3-dihydroxy-1-phenyl-2-propyl)validamine hydrochloride.

Elemental analysis, for $C_{16}H_{25}NO_6 \cdot HCl \cdot H_2O$: Calcd. (%): C, 50.32; H, 7.39; N, 3.67; Cl, 9.29; Found (%): C, 49.86; H, 7.35; N, 3.79; Cl, 9.84.

$[\alpha]_D^{25} + 35.5°$ (c=1, $H_2O$).
TLC: Rf=0.61.

EXAMPLE 4

N-(β-hydroxyphenetyl)validamine hydrochloride 2.0 g of validamine as well as 3.0 g of phenylglyoxal-monohydrate are dissolved in 20 ml of methanol under warming at 60° C., and 5.0 g of magnesium sulfate is added to the solution at room temperature, followed by stirring for 20 hours. The reaction solution is filtered, and the filtrate is concentrated under reduced pressure to distill off the methanol. Ethyl ether is added to the residue, and the resultant precipitate is recovered by filtration. 4.1 g of the Schiff's base thus obtained is dissolved in 25 ml of methanol, and 1.25 g of sodium borohydride is added to the solution under ice-cooling, followed by further stirring at room temperature for 3 hours. Acetone and water are added to the reaction solution, and the solution are concentrated under reduced pressure azeotropically with n-butyl alcohol. The resultant water layer is adjusted to pH 2, washed with ethyl acetate and concentrated under reduced pressure. The concentrated water layer is adjusted to pH 2.8 and chromatographed on a column (250 ml) of MCI Gel CHP20P (produced by Mitsubishi Chemical Ind., Ltd.), followed by the elution with water. The eluate is concentrated under reduced pressure and lyophilized to give 1.2 g of white powder of N-(β-hydroxyphenetyl)validamine hydrochloride.

Elemental analysis, for $C_{15}H_{23}NO_5 \cdot HCl \cdot \frac{1}{2}H_2O$: Calcd. (%): C, 52.55; H, 7.35; N, 4.09; Cl, 10.34; Found (%): C, 52.54; H, 7.57; N, 4.16; Cl, 10.08.

$[\alpha]_D^{25} + 37.6°$ (c=1, $H_2O$).
TLC: Rf=0.67.

EXAMPLE 5

N-(3-phenylpropyl)validamine hydrochloride 2.0 g of validamine is dissolved in 20 ml of methanol under warming in a hot water bath, of 2.7 g of β-phenylpropionaldehyde is added to the solution, followed by stirring at room temperature for 2 hours. The reaction solution is concentrated under reduced pressure, and ethyl ether is added to the residue. The resultant precipitates are recovered by filtration and dried. 2.7 g of the Schiff's base obtained is dissolved in 20 ml of methanol, and 340 mg of sodium borohydride is added to the solution under ice-cooling, followed by stirring for 1 hour. Water and acetone are added to the reaction solution, and the mixture is concentrated under reduced pressure azeotropically with n-butyl alcohol. The resultant aqueous solution is adjusted to pH 2 with 2N-hydrochloric acid and washed with ethyl acetate. The water layer is concentrated under reduced pressure to about 30 ml and chromatographed on a column (250 ml) of MCI Gel CHP20P (produced by Mitsubishi Chemcical Ind., Ltd.), followed by the elution with water. The eluate is concentrated under reduced pressure and lyophilized to give 1.0 g of white powder of N-(3-phenylpropyl)validamine hydrochloride.

Elemental analysis, for $C_{16}H_{25}NO_4 \cdot HCl \cdot \frac{1}{2}H_2O$: Calcd. (%) C, 56.42; H, 7.99; N, 4.11; Cl, 10.41; Found (%): C, 56.84; H, 8.07; N, 4.00; Cl, 11.16.

$[\alpha]_D^{25} + 48.1°$ (c=1, $H_2O$).
TLC: Rf=0.70.

EXAMPLE 6

N-(3-phenoxypropyl)validamine 3.0 g validamine is dissolved in a mixed solution of 60 ml of methanol and 40 ml of dioxane with stirring, and 5.0 g of sodium hydrogen carbonate is added to the solution. Then, 8.6 g of 3-bromo-1-phenoxypropane is added to the mixture under stirring, followed by stirring at 70° C. for 16 hours. The reaction solution is filtered, and the filtrate is concentrated to dryness under reduced pressure. 100 ml of water is added to the residue, and the mixture is adjusted to pH 2 and washed with ethyl acetate. The water layer is adjusted to pH 10 and extracted with n-butyl alcohol. The n-butyl alcohol extract is concentrated under reduced pressure azeotropically with water, and there separates out crystals of N-(3-phenoxypropyl)validamine. Yield of 2.4 g.

Elemental analysis, for $C_{16}H_{25}NO_5$: Calcd. (%): C, 61.71; H, 8.09; N, 4.50; Found (%): C, 61.50; H, 8.17; N, 4.51.

$[\alpha]_D^{25} + 42.7°$ (c=1, $CH_3OH$).
TLC: Rf=0.63.

EXAMPLE 7

N-(3,5-di-tert-butyl-4-hydroxybenzyl)validamine

Dissolved in 60 ml of methanol with stirring are 6.0 g of validamine and 14.0 g of 3,5-di-tert-butyl-4-hydroxybenzaldehyde, and the solution is stirred at 40° C. for 3 hours. The reaction solution is concentrated under reduced pressure, and petroleum ether is added to the residue. The resultant precipitates are recovered by filtration and dried. The Schiff's base obtained is dissolved in 100 ml of methanol, and 1.6 g of sodium borohydride is added to the solution with stirring under ice-cooling, followed by stirring at room temperature for 40 minutes. The reaction solution is concentrated to dryness under reduced pressure, and the residue is suspended in 200 ml of water, and the suspension is adjusted to pH 2 and washed with ethyl acetate. The water layer is adjusted to pH 10 and extracted with ethyl acetate. The ethyl acetate extract is washed with water and concentrated under reduced pressure. Ethyl ether is added to the residue, and the resultant precipitates are recovered by filtration to give 2.3 g of crude powder. The crude powder is suspended in 50 ml of water, and the suspension is adjusted to pH 2 to make a solution. The solution is chromatographed on a column of MCI Gel CHP20P (250 ml, produced by Mitsubishi Chemical Ind., Ltd.), and the column is washed with water, followed by the elution with a gradient of water-methanol. The eluate is concentrated to dryness under reduced pressure, and 100 ml of water and 50 ml of ethyl acetate are added to the residue. The water layer is adjusted to pH 10 and stirred, and then, the ethyl acetate layer is separated. The water layer is further extracted with two portions of 50 ml of ethyl acetate, and the ethyl acetate extracts are combined, washed with water and concentrated under reduced pressure to give 2.1 g of N-(3,5-di-tert-butyl-4-hydroxybenzyl)-validamine.

Elemental analysis, for $C_{22}H_{37}NO_5$: Calcd. (%): C, 66.80; H, 9.43; N, 3.54; Found (%): C, 66.90; H, 9.70; N, 3.31.

$[\alpha]_D^{25} + 66.1°$ (c=1, $CH_3OH$).
TLC: Rf=0.83.

EXAMPLE 8

N-furfurylvalidamine 2.0 g of validamine and 2 ml of 2-furaldehyde in 20 ml of methanol are stirred at 60° C. for 30 minutes and further at room temperature for 1.5 hours. The reaction solution is concentrated under reduced pressure, and ethyl ether is added to the residue. The resultant precipitates are recovered by filtration and dried. 2.45 g of the Schiff's base thus obtained is dissolved in 30 ml of methanol, and 340 mg of sodium borohydride is added to the solution under ice-cooling, followed by stirring at the same temperature for 3 hours. To the reaction solution are added water, acetone and n-butyl alcohol, and the mixture is concentrated under reduced pressure to distill off the organic solvent. The resultant aqueous solution is chromatographed on a column (250 ml) of MCI Gel CHP20P (produced by Mitsubishi Chemical Ind., Ltd.), and the column is washed with water, followed by the elution with a gradient of water—80% aqueous methanol. The eluate is concentrated under reduced pressure and lyophilized to give 2.1 g of N-furfurylvalidamine.

Elemental analysis, for $C_{12}H_{19}NO_5$: Calcd. (%): C, 56.02; H, 7.44; N, 5.44; Found (%): C, 55.81; H, 7.58; N, 5.45.

$[\alpha]_D^{25} + 81.7°$ (c=1, $H_2O$).
TLC: Rf=0.54.

EXAMPLE 9

N-(3-pyridylmethyl)validamine 3.0 g of validamine is dissolved in 30 ml of methanol under warming, and 1.8 ml of nicotinaldehyde is added to the solution, followed by stirring at 60° C. for 1 hours. The reaction solution is concentrated under reduced pressure, and ethyl ether is added to the residue. The supernatant solution is discarded by decantation, and the resultant precipitates are collected and dried. 4.5 g of the Schiff's base obtained is dissolved in 30 ml of methanol, and 800 mg of sodium borohydride is added to the solution under ice-cooling, followed by stirring at the same temperature for 1 hour and further at room temperature for 1 hour. To the reaction solution are added water, acetone and n-butyl alcohol, and the mixture is concentrated under reduced pressure. The resultant aqueous solution is chromatographed on a column (250 ml) of MCI Gel CHP20P (produced by Mitsubishi Chemical Ind., Ltd.), and the elution is conducted with a gradient of water—80% aqueous methanol. The eluate is concentrated under reduced pressure, and the concentrate is chromatographed on a column (250 ml) of Dowex 1×2 (OH⁻ type), followed by the elution with water. The eluate is concentrated under reduced pressure and lyophilized to give 3.6 g of N-(3-pyridylmethyl)validamine.

Elemental analysis, for $C_{13}H_{20}N_2O_4$: Calcd. (%): C, 58.19; H, 7.51; N, 10.44; Found (%): C, 58.28; H, 7.65; N, 10.47.

$[\alpha]_D^{25} + 81.3°$ (c=1, $H_2O$).
TLC: Rf=0.18.

EXAMPLE 10

N-thenylvalidamine 2.0 g of validamine is dissolved in 20 ml of methanol in a hot water bath, and 2.0 ml of thiophenecarbaldehyde is added to the solution, followed by stirring at room temperature for 1.5 hours. The reaction solution is concentrated under reduced pressure, and 300 ml of ethyl ether is added to the residue. The resultant precipitates are recovered by filtration and dried. 2.7 g of the Schiff's base obtained is dissolved in 30 ml of methanol, 420 mg of sodium borohydride is added little by little to the solution under ice-cooling, followed by stirring at the same temperature for 1 hour. To the reaction solution are added ice-cold water, acetone and n-butyl alcohol, and the mixture is concentrated under reduced pressure to distill off the organic solvent. The concentrate is added to a column of 250 ml of MCI Gel CHP20P (produced by Mitsubishi Chemical Ind., Ltd.), and the column is washed with water, followed by the elution with a gradient of water—80% aqueous methanol. The eluate is concentrated under reduced pressure and lyophilized to give N-thenylvalidamine. Yield of 2.4 g.

Elemental analysis, for $C_{12}H_{19}NO_4S$: Calcd. (%): C, 52.73; H, 7.01; N, 5.12; S, 11.73; Found (%): C, 52.40; H, 7.26; N, 5.20; S, 12.10.

$[\alpha]_D^{25} + 82.3°$ (c=1, $H_2O$).
TLC: Rf=0.59.

EXAMPLE 11

N-(cyclohexylmethyl)validamine

In 80 ml of dimethylformamide is dissolved 3.0 g of validamine, and 5.0 g of sodium hydrogen carbonate and 4 ml of cyclohexylmethylbromide are added to the solution, followed by stirring at 60° to 65° C. for 40 hours. The reaction solution is filtered, and the filtrate is concentrated under reduced pressure. Water is added to the residue, and the mixture is adjusted to pH 2 and washed with toluene. The water layer is adjusted to pH 10 and extracted with three portions of n-butyl alcohol. The n-butyl alcohol extracts are combined, washed once with water and concentrated under reduced pressure azeotropically with water. The residue is dissolved in ethanol, and the solution is concentrated under reduced pressure. Ethyl ether is added to the residue to give crystals of N-(cyclohexylmethyl)validamine. Yield of 1.4 g.

Elemental analysis, for $C_{14}H_{27}NO_4$: Calcd. (%): C, 61.51; H, 9.96; N, 5.12; Found (%): C, 61.19; H, 9.65; N, 5.16.

$[\alpha]_D^{25} + 59.0°$ (c=1, $H_2O$).
TLC: Rf=0.66.

EXAMPLE 12

N-geranylvalidamine sulfate

In 80 ml of dimethylformamide is dissolved 3.0 g of validamine, and 5.0 g of sodium hydrogen carbonate and 8 ml of geranyl chloride are added to the solution, followed by stirring at room temperature for 40 hours. The reaction solution is filtered, and the filtrate is concentrated under reduced pressure. Water is added to the residue, and the mixture is adjusted to pH 2 and washed with toluene. The water layer is adjusted to pH 10 and extracted with n-butyl alcohol. The n-butyl alcohol extracts are combined, washed once with water and concentrated under reduced pressure azeotropically with water. The residue is suspended in water, and the suspension is adjusted to pH 2 with 1N sulfuric acid to make a solution. The solution is chromatographed on a column (250 ml) of MCI Gel CHP20P (produced by Mitsubishi Chemical Ind., Ltd.), and the column is washed with water, followed by the elution with a gradient of water-methanol. The eluate is collected, concentrated under reduced pressure, and the resultant aqueous solution is lyophilized. Yield of 2.4 g.

Elemental analysis, for $C_{17}H_{31}NO_4 \cdot \frac{1}{2}H_2SO_4 \cdot \frac{1}{2}H_2O$: Calcd.(%): C, 54.96; H, 8.95; N, 3.77; S, 4.31; Found (%): C, 54.90; H, 9.35; N, 3.84; S, 4.63.

$[\alpha]_D^{25}+45.2°$ (c=1, $H_2O$).
TLC: Rf=0.77.
$IC_{50}$ (saccharase): $7.9 \times 10^{-7}$M.

EXAMPLE 13

N-(4-carboxybenzyl)validamine 2.0 g of validamine is dissolved in 20 ml of methanol under warming in a hot water bath, and to the solution are added 3.0 g of 4-carboxybenzaldehyde, 2.8 ml of triethylamine and 5.0 g of magnesium sulfate, followed by stirring at room temperature for 3 hours. The reaction mixture is filtered, and the filtrate is concentrated to dryness under reduced pressure. The residue is dissolved in 25 ml of methanol, and 700 mg of sodium borohydride is added to the solution under ice-cooling, followed by stirring at the same temperature for 1 hour. 300 ml of water is added to the reaction solution and the mixture is concentrated under reduced pressure to about 200 ml. The concentrate is adjusted to pH 2 and washed with ethyl acetate. The water layer is adjusted to pH 4.5, and concentrated under reduced pressure to about 50 ml. The concentrate is chromatographed on a column (250 ml) of activated carbon (produced by Takeda Chemical Ind., Ltd., Japan), and the column is washed with water, followed by the elution with a gradient of water-methanol. The eluate is concentrated under reduced pressure and lyophilized to give 2.0 g of N-(4-carboxybenzyl)validamine.

Elemental analysis, for $C_{15}H_{21}NO_6 \cdot H_2O$: Calcd.(%): C, 54.70; H, 7.04; N, 4.25; Found (%): C, 54.51; H, 7.13; N, 4.26.

$[\alpha]_D^{25}+55.0°$ (c=1, $H_2O$).
TLC: RF=0.59.

EXAMPLE 14

N-(D-gluco-2,3,4,5,6-pentahydroxyhexyl)validamine

In 30 ml of dimethylformamide are suspended 2.62 of validamine and 4.1 g of d-glucose, and the suspension is stirred at 37° C. for 63 hours. 350 ml of acetone is added to the reaction solution, and the resultant precipitates are recovered by filtration. The precipitates are dissolved in 150 ml of water, and 1.2 g of sodium borohydride is added little by little to the solution under ice-cooling, followed by stirring at the same temperature for 2 hours. The mixture is adjusted to pH 4 by addition of acetic acid and added for adsorption to a column of Dowex 50W×8 (H+ type, 150 ml). After the column is washed with water, the elution is conducted with 0.5N aqueous ammonia. The eluate is concentrated under reduced pressure, and the residue is chromatographed on a column (750 ml) of Dowex 1×2 (OH− type) (produced by Dow Chemical Co.), followed by the elution with water. The eluate is concentrated under reduced pressure and lyophilized to give N-(D-gluco-2,3,4,5,6-pentahydroxyhexyl)validamine. Yield of 3.1 g.

Elemental analysis, for $C_{13}H_{27}NO_9 \cdot H_2O$: Calcd.(%): C, 43.45; H, 8.13; N, 3.90; Found (%): C, 43.69; H, 8.22; N, 3.94.

$[\alpha]_D^{25}+41.6°$ (c=1, $H_2O$).
TLC: Rf=0.23.

EXAMPLE 15

N-(D-xylo-2,3,4,5-tetrahydroxypentyl)validamine

In 30 ml of dimethylformamide are suspended 2.65 g of validamine and 3.5 g of D-xylose, and the suspension is stirred at 40° C. for 42 hours. 300 ml of acetone is added to the reaction solution, and the resultant precipitates are collected by filtration, washed with acetone and dried. The precipitates are dissolved in 150 ml of water, and 1.2 g of sodium borohydride is added little by little to the solution under ice-cooling, followed by stirring at the same temperature for 5 hours. The reaction solution is made acid with acetic acid and added for adsorption to a column of Dowex 50W×8 (H+ type, 150 ml). After the column is washed with water, the elution is conducted with 0.5N aqueous ammonia, and the eluate is concentrated under reduced pressure. The residue is chromatographed on a column (270 ml) of Dowex 1×2 (OH− type) (produced by Dow Chemical Co.), and the elution is conducted with water. The eluate is concentrated under reduced pressure and lyophilized to give N-(D-xylo-2,3,4,5-tetrahydroxypentyl)validamine. Yield of 2.5 g.

Elemental analysis, for $C_{12}H_{25}NO_8 \cdot H_2O$: Calcd.(%): C, 43.76; H, 8.26; N, 4.25; Found (%): C, 43.86; H, 8.16; N, 4.12.

$[\alpha]_D^{25}+44.4°$(c=1, $H_2O$).
TLC: RF=0.23.

EXAMPLE 16

N-(L-xylo-2,3,4,5-tetrahydroxy-1-hydroxymethylpentyl)validamine

In 125 ml of dimethylsulfoxide are dissolved 5.0 g of validamine and 11.0 g of L-sorbose, and 3.75 ml of 2N hydrochloric acid and then 6.4 g of sodium borohydride are added successively to the solution, followed by stirring at 60 to 70° C. for 45 hours. The reaction solution is concentrated under reduced pressure, and the residue is dissolved in 300 ml of water and passed through a column of Amberlite CG-50 (NH4+ type, 450 ml). After the column is washed with water, the effluent solution and washings are combined and added for adsorption to a column of Dowex 50W×8 (H+ type, 150 ml) After the column is washed with water, the elution is conducted with 0.5N aqueous ammonia. The eluate is concentrated under reduced pressure, and the residue is added to a column (270 ml) of Dowex 1×2 (OH− type) (produced by Dow Chemical Co.), followed by the elution with water. The eluate is concentrated under reduced pressure and lyophilized to give N-(L-xylo-2,3,4,5-tetrahydroxy-1-hydroxymethylpentyl)validamine. Yield of 1.5 g.

Elemental analysis, for $C_{13}H_{27}NO_9 \cdot \frac{1}{2}H_2O$: Calcd.(%): C, 44.56; H, 8.06; N, 4.00; Found (%): C, 44.43; H, 8.25; N, 3.91.

$[\alpha]_D^{25}+65.7°$ (c=1, $H_2O$).
TLC: Rf=0.27.
$IC_{50}$ (saccharase): $7.9 \times 10^{-8}$M.

EXAMPLE 17

N-(β-hydroxyphenetyl)validamine and N-[α-(hydroxymethyl)benzyl]validamine

In 150 ml of methanol are dissolved 5.0 g of validamine and 6 ml of styrene oxide, and the solution is heated under reflux. After 4 hours, 5 ml of sytrene oxide is further added, and the mixture is furthermore heated under reflux for 4 hours. The reaction solution is concentrated under reduced pressure, and the residue is partitioned between water and ethyl acetate. The water layer is separated, concentrated under reduced pressure and chromatographed on a column of Dowex 50W×8 (H+ type, 150 ml, produced by Dow Chemical Co.). After the column is washed with water, elution is conducted with 0.5N aqueous ammonia. The eluate is concentrated under reduced pressure, and the residue is chromatographed on a column of Amberlite CG-50 (NH$_4$+ type, 3 l, produced by Rohm & Haas Co.), and elution with water allows separation into two components. The first eluate is concentrated under reduced pressure and lyophilized to give white powder (1.7 g) of N-[α-(hydroxymethyl)benzyl]validamine, while the subsequent eluate is concentrated under reduced pressure and lyophilized to give N-(β-hydroxyphenetyl)-validamine (4.7 g).

N-(β-hydroxyphenetyl)validamine

Elemental analysis, for $C_{15}H_{23}NO_5 \cdot \frac{1}{2}H_2O$: Calcd.(%): C, 58.81; H, 7.90; N, 4.57; Found (%): C, 59.21; H, 8.16; N, 4.69.

$[\alpha]_D^{27} + 58.6°$ (c=1, H$_2$O).

TLC: Rf=0.67.

N-[α-(hydroxymethyl)benzyl]validamine

Elemental analysis, for $C_{15}H_{23}NO_5$: Calcd.(%): C, 60.59; H, 7.80; N, 4.71; Found (%): C, 60.33; H, 8.29; N, 4.87.

$[\alpha]_D^{27} + 70.6°$ (c=1, H$_2$O).

TLC: Rf=0.63.

IC$_{50}$(maltase): $4.5 \times 10^{-6}$M.

EXAMPLE 18

N-(2-hydroxy-3-phenoxypropyl)validamine

A 4.7 g quantity of phenol is dissolved in an aqueous solution (10 ml) of 2.2 g of sodium hydroxide under a stream of nitrogen, and 5 g of epichlorohydrin is added to the solution, followed by stirring at room temperature for 24 hours. 50 ml of water is added to the reaction solution, and the mixture is extracted with two 50 ml portions of dichloromethane. The dichloromethane layer is washed with water, dried over anhydrous sodium sulfate and freed of the solvent to give about 7 g of a mixture of 1-phenoxy-2,3-epoxypropane and 1-chloro-2-hydroxy-3-phenoxypropane.

2.0 g of validamine is dissolved in 80 ml of N,N-dimethylformamide, and 5.7 g of sodium hydrogen carbonate is added to the solution. Then, about 7 g of the above mixture of 1-phenoxy-2,3-epoxypropane and 1-chloro-2-hydroxy-3-phenoxypropane is added to the mixture, followed by stirring overnight at 90° C. (the bath temperature). The reaction solution is filtered, and the filtrate is concentrated under reduced pressure. Water and n-butyl alcohol are added to the residue, and the mixture is adjusted to pH 2 with 2N hydrochloric acid and then partitioned between them. The water layer is separated, concentrated under reduced pressure and chromatographed on a column of MCI Gel CHP20P (250 ml, produced by Mitsubishi Chemical Ind., Ltd.), followed by elution with water. The eluate is concentrated under reduced pressure and lyophilized to give 1.7 g of white powder of N-(2-hydroxy-3-phenoxypropyl)-validamine hydrochloride.

Elemental analysis, for $C_{16}H_{25}NO_6 \cdot HCl \cdot \frac{1}{2}H_2O$: Calcd. (%): C, 51.54; H, 7.30; N, 3.76; Cl, 9.51; Found (%): C, 51.10; H, 7.53; N, 4.25; Cl, 10.00.

$[\alpha]_D^{23} + 43.0°$ (c=1, H$_2$O).

TLC: Rf=0.66.

IC$_{50}$(maltase): $3.4 \times 10^{-6}$M.

EXAMPLE 19

N-(D-arabino-2,3,4,5-tetrahydroxy-1-hydroxymethylpentyl)validamine

In 75 ml of dimethylformamide are dissolved 3.0 g of validamine and 6.6 g of D-fructose. After the addition of 2.2 ml of 2N hydrochloric acid, 3.8 g of sodium cyanoborohydride is added to the mixture, followed by stirring at 60° to 70° C. for 40 hours. The reaction solution is concentrated under reduced pressure, and the residue is dissolved in water. The solution is made acid (pH 0.5 or lower) with 2N HCl, stirred until the evolution of gas ceases, adjusted to pH 4.5 with N-sodium hydroxide and concentrated under reduced pressure. The concentrate is chromatographed on a column of Dowex 50W×8 (H+ type, 300 ml, produced by Dow Chemical Co.), and after the column is washed with water, elution is conducted with 0.5N aqueous ammonia. The eluate is concentrated under reduced pressure, and the residue is chromatographed on a column of Dowex 1×2 (OH− type, 450 ml), followed by elution with water. The eluate is concentrated under reduced pressure and lyophilized to give 2.7 g of N-(D-arabino-2,3,4,5-tetrahydroxy-1-hydroxymethylpentyl)validamine.

Elemental analysis, for $C_{13}H_{27}NO_9$: Calcd. (%): C, 45.74; H, 7.94; N, 4.10; Found (%): C, 45.38; H, 8.46; N, 4.14.

$[\alpha]_D^{27} + 70.1°$ (c=1, H$_2$O).

TLC: Rf=0.29.

IC$_{50}$(maltase): $5.9 \times 10^{-7}$M.

EXAMPLE 20

N-(2-hydroxycyclohexyl)validamine

In 100 ml of methanol is dissolved 2.0 g of validamine, and 6 ml of 1,2-epoxycyclopentane is added to the solution, followed by heating under reflux with stirring for 9 hours. The reaction solution is concentrated under reduced pressure, and ethyl ether is added to the residue. The resultant precipitates are chromatographed on a column of Amberlite CG-50 (NH$_4$+ type, produced by Rohm & Haas Co., 400 ml), and elution is conducted with water. The eluate (19 g each, fraction Nos. 26–60) is concentrated under reduced pressure and lyophilized to give 1.1 g of white powder of N-(2-hydroxycyclohexyl)validamine.

$[\alpha]_D^{24} + 61.1°$ (c=1, H$_2$O).

Elemental analysis, for $C_{13}H_{25}NO_5 \cdot \frac{1}{2}H_2O$: calcd. (%): C, 54.91; H, 9.22; N, 4.93; Found (%): C, 55.12; H, 9.39; N, 4.82.

TLC: Rf=0.52.

IC$_{50}$(saccharase): $9.6 \times 10^{-8}$M.

EXAMPLE 21

N-(2-hydroxycyclopentyl)validamine

In 100 ml of methanol is dissolved 2.0 g of validamine, and 6 ml of 1,2-epoxycyclopentane is added to the solution, followed by heating under reflux for 24 hours. The reaction solution is concentrated under reduced pressure, and ethyl ether is added to the residue. The resultant precipitates are chromatographed on a column of Amberlite CG-50 ($NH_4^+$ type, produced by Rohm & Haas, 400 ml), and elution is conducted with water. The eluate (each 19 g, fraction Nos. 27–45) is concentrated under reduced pressure and lyophilized to give 0.7 g of white powder of N-(2-hydroxycyclopentyl)validamine. $[\alpha]_D^{24}+70.1°$ (c=1, $H_2O$).

Elemental analysis, for $C_{12}H_{23}NO_5 \cdot \frac{1}{2}H_2O$: Calcd. (%): C, 53.32; H, 8.95; N, 5.18; Found (%): C, 53.33; H, 9.28; N, 5.18.

TLC: Rf=0.49.

$IC_{50}$(saccharase): $1.3 \times 10^{-7}$M.

EXAMPLE 22

N-(1,3-dihydroxy-2-propyl)valiolamine

To a solution of 2.0 g of valiolamine in 50 ml of N,N-dimethylformamide are added 3.4 g of dihydroxyacetone, 1.5 ml of 2N hydrochloric acid and 2.6 g of sodium cyanoborohydride, followed by stirring at 60° to 70° C. for 16 hours. The reaction solution is concentrated under reduced pressure to distill off the N,N-dimethylformamide as much as possible, and the residue is dissolved in 100 ml of water. The solution is made acid with 2N hydrochloric acid, stirred for 30 to 40 minutes under ice-cooling, adjusted to pH 4.5 with 1N sodium hydroxide solution and subjected to column chromatography (250 ml) on Dowex 50W×8 type) (produced by Dow Chemical of the United States of America). After the washing with water, the elution is carried out with 0.5N aqueous ammonia. The eluate is concentrated under reduced pressure, and the concentrate is chromatographed on a column (250 ml) of Amberlite CG-50 ($NH_4^+$ type) (produced by Rohm & Haas Co. of the United States of America), followed by the elution with water. The eluate is concentrated under reduced pressure, and the concentrate is lyophilized to give 2.0 g of white powder of N-(1,3-dihydroxy-2-propyl)valiolamine.

Elemental analysis, for $C_{10}H_{21}NO_7 \cdot \frac{1}{2}H_2O$: Calcd. (%): C, 43.46; H, 8.03; N, 5.07; Found (%): C, 43.56; H, 8.36; N, 5.00.

$[\alpha]_D^{26}+27.2°$ (c=1, $H_2O$).

NMR ($D_2O$)δ: 1.65 (1H, dd, J=3 and 15.5), 2.23 (1H, dd, J=3.5 and 15.5), 3.01 (1H, quin, J=5), 3.5 to 4.2 (10H).

Ethanol (abbout 60 ml) is added to the above lyophilized product (1.2 g) of N-(1,3-dihydroxy-2-propyl)valiolamine, and the mixture is warmed for 30 minutes in a hot water bath (the bath temperature: 90°–95° C.), followed by leaving on standing in a refiegerator. The resultant crystalline substance is recovered by filtration, washed with ethanol and then dried in a desiccator under reduced pressure. Yield of 0.95 g.

Elemental analysis, for $C_{10}H_{21}NO_7$: Calcd. (%): C, 44.93; H, 7.92; N, 5.24; Found (%): C, 44.62; H, 7.79; N, 5.09.

$[\alpha]_D^{25}+26.2°$ (c=1, $H_2O$).

TLC: Rf=0.29.

EXAMPLE 23

N-(β-hydroxyphenetyl)valiolamine and N-[α-(hydroxymethyl)benzyl]valiolamine

In 500 ml of methanol are dissolved 10 g of valiolamine and 12 ml of styrene oxide. After the solution is refluxed with stirring for 4 hours, 12 ml of styrene oxide is added, and the mixture is further heated under reflux with stirring for 6 hours. The reaction solution is concentrated under reduced pressure, and the residue is partitioned between water and ethyl acetate, and the water layer is separated. The water layer is concentrated under reduced pressure, and the residue is chromatographed on a column of Amberlite CG-50 ($NH_4^+$ type, 1.6 l) (produced by Rohm & Haas Co.). The elution is carried out with water and three eluted fractions (fraction 1; 1–1.2 l, fraction 2; 1.2–1.7 l, fraction 3; 1.7–3.4 l) are obtained. Each of these eluted fractions purified by repeating once more the same chromatographic procedure, concentrated under reduced pressure and lyophilized to give, in the order of the elution in the first column chromatography, first N-[α-(hydroxymethyl)benzyl]valiolamine (3.7 g), then an isomer of N-(β-hydroxyphenetyl)valiolamine showing $[\alpha]_D^{24}-11°$ (c=1, $H_2O$) and finally an isomer of N-(β-hydroxyphenetyl)valiolamine showing $[\alpha]_D^{24}+17°$ (c=1, $H_2$) (4.3 g).

N-[α-(hydroxymethyl)benzyl]valiolamine obtained by the above procedure is dissolved in water under heating with stirring, and the solution, on standing under ice-cooling, affords an isomer with $[\alpha]_D^{24}-10.6°$ (c=1, $H_2O$) in the form of crystals. On the other hand, the mother liquor is concentrated under reduced pressure, and the concentrate is lyophilized to give a white powder showing $[\alpha]_D^{24}+26.5°$ (c=1, $H_2O$). N-(β-hydroxyphenetyl)valiolamine (optical isomer showing $[\alpha]_D^{24}-11°$): TLC: Rf=0.63.

Elemental analysis, for $C_{15}H_{23}NO_6 \cdot \frac{1}{2}H_2O$: Calcd.(%): C, 56.68; H, 7.45; N, 4.41; Found (%): C, 56.86; H, 7.65; N, 4.68.

NMR ($D_2O$)δ: 1.56 (1H, dd, J=3 and 15.5), 2.17 (1H, dd, J=3.5 and 15.5), 2.91 (1H, dd, J=8 and 12.5), 3.19 (1H, dd, J=5, 12.5), 3.20–4.05 (6H), 4.97 (1H, dd, J=5 and 8), 7.60 (5H, s).

N-(β-hydroxyphenetyl)valiolamine (optical isomer showing $[\alpha]_D^{24}+17°$): TLC: Rf=0.62.

Elemental analysis, for $C_{15}H_{23}NO_6 \cdot \frac{1}{2}H_2O$: Calcd.(%): C, 56.68; H, 7.45; N, 4.41; Found (%): C, 56.75; H, 7.43; N, 4.50.

NMR ($D_2O$)δ: 1.57 (1H, dd, J=3 and 15.5), 2.19 (1H, dd, J=3.5 and 15.5), 2.95 (1H, dd, J=5 and 12.5), 3.20 (1H, dd, J=8 and 12.5), 3.2 to 4.05 (6H), 5.01 (1H, dd, J=5 and 8), 7.60 (5H, s).

N-[α-(hydroxymethyl)benzyl]valiolamine (optical isomer showing $[\alpha]_D^{24}-10.6°$): TLC: Rf=0.59.

Elemental analysis, for $C_{15}H_{23}NO_6 \cdot \frac{1}{2}H_2O$: $IC_{50}$ (saccharase): $6.6 \times 10^{-9}$M, $IC_{50}$ (maltase): $1.3 \times 10^{-8}$M Calcd.(%): C, 56.68; H, 7.45; N, 4.41; Found (%): C, 56.76; H, 7.81; N, 4.58.

NMR ($D_2O$)δ: 1.43 (1H, dd, J=3 and 15), 1.73 (1H, dd, J=3.5 and 15), 3.2 to 4.1 (9H), 7.58 (5H, s).

N-[α-(hydroxymethyl)benzyl]valiolamine (white powder showing $[\alpha]_D^{24}+26.5°$ (c=1, $H_2O$)).

TLC: Rf=0.61.

Elemental analysis, for $C_{15}H_{23}NO_6 \cdot \frac{1}{2}H_2O$: Calcd.(%): C, 55.89; H, 7.50; N, 4.35; Found (%): C, 55.88; H, 7.60; N, 4.43.

EXAMPLE 24

N-(β-hydroxyphenetyl)valiolamine

In 20 ml of methanol are dissolved 1.0 g of valiolamine and 1.5 g of phenylglyoxal monohydrate, and 2.5 g of magnesium sulfate is added to the solution, followed by stirring at room temperature for 20 hours. The reaction solution is filtered, and the filtrate is concentrated under reduced pressure to distill off the methanol. Ethyl ether is added to the residue, and the resultant precipitates are recovered by filtration and dried. 1.1 g of the obtained Schiff's base is dissolved in 20 ml of methanol, and 400 mg of sodium borohydride is added to the solution under ice-cooling, followed by stirring for 3 hours. Water, acetone and n-butyl alcohol are added to the reaction solution, and the mixture is concentrated under reduced pressure. The resultant aqueous solution is adjusted to pH 2 and washed with ethyl acetate. The water layer is concentrated under reduced pressure and the concentrate is chromatographed on a column of MCI Gel CHP20P (180 ml), followed by the elution with water.

The elute is adjusted to pH 10 with 1N sodium hydroxide solution and then concentrated under reduced pressure to about 20 ml. The concentrate is chromatographed on a column (180 ml) of Amberlite CG-50 ($NH_4^+$ type) (produced by Rohm & Haas Co.) and, when elution is conducted with water, N-(β-hydroxyphenetyl)valiolamine is separated into two optical isomers. The first eluted fraction (180–250 ml) is concentrated under reduced pressure and lyophilized to give an isomer showing $[\alpha]_D^{26} -9.3°$ (c=1, $H_2O$), while the subsequently eluted one (300–420 ml) is concentrated under reduced pressure and lyophilized to give an isomer showing $[\alpha]_D^{26} +15.8°$ (c=1, $H_2O$).

EXAMPLE 25

N-(D-gluco-2,3,4,5,6-pentahydroxyhexyl)valiolamine

In 9 ml of N,N-dimethylformamide are suspended 1.0 g of valiolamine and 1.5 g of D-glucose, and the suspension is stirred at 37° C. for 65 hours. 90 ml of acetone is added to the reaction solution, and the resultant precipitates are recovered by filtration. 2.5 g of the Schiff's base thus obtained is dissolved in 50 ml of water, and 800 mg of sodium borohydride is added to the solution under ice-cooling, followed by stirring at the same temperature for 2 hours. The reaction solution is adjusted to pH 4 and added for adsorption to a column of Dowex 50W×8 ($H^+$ type, 75 ml) (produced by Dow Chemical Co.). After the column is washed with water, the elution is conducted with 0.5N aqueous ammonia. The eluate is concentrated under reduced pressure, and the residue is chromatographed on a column (250 ml) of Dowex 1×2 ($OH^-$ type) (produced by Dow Chemical Co.), followed by the elution with water. The eluate is concentrated under reduced pressure and lyophilized to give N-(D-gluco-2,3,4,5,6-pentahydroxyhexyl)valiolamine. Yield of 1.6 g.

Elemental analysis, for $C_{13}H_{27}NO_{10} \cdot \frac{1}{2}H_2O$: Calcd.(%): C, 42.61; H, 7.70; N, 3.82; Found (%): C, 42.54; H, 7.83; N, 3.83.

$[\alpha]_D^{26} -9.0°$ (c=1, $H_2O$).
TLC: Rf=0.19.

EXAMPLE 26

N-(L-xylo-2,3,4,5-tetrahydroxy-1-hydroxymethylpentyl)valiolamine

In 50 ml of N,N-dimethylformamide are dissolved 2.0 g of valiolamine and 4.4 g of L-sorbose, and 1.5 ml of 2N hydrochloric acid and 2.6 g of sodium cyanoborohydride are added to the solution, followed by stirring at 60° to 70° C. for 45 hours. As much as reaction solvent as possible is distilled off under reduced pressure, and the residue is dissolved in 100 ml of water. 150 ml of Dowex 50W×8 ($H^+$ type) (produced by Dow Chemical Co.) is added to the solution, and the mixture is stirred at room temperature for 30 minutes. The above mixture of the aqueous solution and ion exchange resin is poured in a chromatographic column packed with another 150 ml of Dowex 50W×8 ($H^+$ type), and the column is washed with water, followed by the elution with 0.5N aqueous ammonia. The eluates are combined and concentrated under reduced pressure. The concentrate is chromatographed on a column of Amberlite CG-50 ($NH_4^+$ type, 250 ml) (produced by Rohm & Haas Co.), and the elution is conducted with water. The eluates are combined and concentrated under reduced pressure. The concentrate is further chromatographed on a column (250 ml) of Dowex 1×2 ($OH^-$ type) (produced by Dow Chemical Co.), and the elution is conducted with water. The eluate is concentrated under reduced pressure and lyophilized to give N-(L-xylo-2,3,4,5-tetrahydroxy-1-hydroxymethylpentyl)valiolamine. Yield of 375 mg.

Elemental analysis, for $C_{13}H_{27}NO_{10} \cdot \frac{1}{2}H_2O$: Calcd.(%): C, 42.61; H, 7.70; N, 3.82; Found (%): C, 42.74; H, 8.04; N, 3.79.

$[\alpha]_D^{26} +23.8°$ (c=1, $H_2O$).
TLC: Rf=0.23.

EXAMPLE 27

N-geranylvaliolamine

In 55 ml of N,N-dimethylformamide is dissolved 2.0 g of valiolamine, and 3.4 g of sodium hydrogencarbonate and 5.5 ml of geranyl chloride are added to the solution, followed by stirring at room temperature for 48 hours. The reaction solution is filtered, and toluene is added to the filtrate. The solvent is distilled off under reduced pressure, and the residue is treated with water. The mixture is adjusted to pH 2 and washed with ethyl acetate. The water layer is concentrated under reduced pressure, and the concentrate is chromatographed on a column (180 ml) of MCI Gel CHP20P (produced by Mitsubishi Chemical Ind., Ltd.). After the column is washed with water, the elution is conducted with a water-methanol gradient. The eluate is collected and concentrated under reduced pressure. The resultant aqueous solution is lyophilized to gie N-geranylvaliolamine hydrochloride. Yield of 2.3 g.

Elemental analysis, for $C_{17}H_{31}NO_5 \cdot HCl \cdot H_2O$: Calcd.(%): C, 53.18; H, 8.92; N, 3.65; Cl, 9.24; Found (%): C, 52.92; H, 9.18; N, 3.29; Cl, 9.48.

$[\alpha]_D^{26} +17.4°$ (c=1, $H_2O$).
TLC: Rf=0.73.

EXAMPLE 28

N-(cyclohexylmethyl)valiolamine

In 55 ml of dimethylformamide is dissolved 2.0 g of valiolamine, and 3.4 g of sodium hydrogencarbonate and 2.7 ml of cyclohexylmethyl bromide are added to the solution, followed by stirring at 60° to 70° C. for 40 hours. The reaction solution is filtered, and the filtrate is concentrated under reduced pressure. Water (80 ml) and ethyl acetate (80 ml) are added to the residue, and the mixture is adjusted to pH 2 with 2N hydrochloric acid and partitioned. The water layer is separated, washed with ethyl acetate and concentrated under reduced pressure. The concentrate is chromatographed on a column (250 ml) of MCI Gel CHP20P (produced by Mitsubishi Chemical Ind., Ltd.), and the elution is accomplished with water. The eluate is concentrated under reduced pressure, and the concentrate is adjusted to pH 10 with N sodium hydroxide solution and again chromatographed on a column (180 ml) of MCI Gel CHP. After the column is washed with water, the elution is conducted with a water—60% aqueous methanol gradient, and the eluate is concentrated under reduced pressure and lyophilized to give N-(cyclohexylmethyl)-valiolamine. Yield of 220 mg.

Elemental analysis, for $C_{14}H_{27}NO_5$: Calcd.(%): C, 58.11; H, 9.41; N, 4.84; Found (%): C, 58.09; H, 9.66; N, 4.71.

$[\alpha]_D^{26} + 3.3°$ (c=1, $H_2O$).
TLC: Rf=0.61.

EXAMPLE 29

N-phenetylvaliolamine

In 40 ml of methanol is dissolved 2.0 g of valiolamine, and 5 ml of 50% diethyl phthalate solution of phenetylacetaldehyde is added to the solution, followed by stirring at room temperature for 4 hours. The reaction solution is concentrated under reduced pressure, and ethyl ether is added to the residue. The resultant precipitates are recovered by filtration and dried under reduced pressure. The Schiff's base (3.0 g) thus obtained is dissolved in 25 ml of methanol, and 400 mg of sodium borohydride is added to the solution under ice-cooling, followed by stirring for 6 hours. To the reaction solution are added water, acetone and n-butyl alcohol, and then, the organic solvent is distilled off under reduced pressure. The resultant aqueous solution is adjusted to pH 2 and washed with ethyl acetate, and the water layer is then concentrated under reduced pressure. The concentrate is chromatographed on a column (250 ml) of MCI Gel CHP20P (produced by Mitsubishi Cehmical Ind., Ltd.), and the elution is accomplished with water. The eluate is concentrated under reduced pressure and lyophilized to give 1.0 g of N-phenetylvaliolamine hydrochloride.

Elemental analysis, for $C_{15}H_{23}NO_5.HCl.\frac{1}{2}H_2O$: Calcd.(%): C, 52.55; H, 7.35; N, 4.09; Cl, 10.34; Found (%): C, 52.36; H, 7.73; N, 4.13; Cl, 10.83.

$[\alpha]_D^{26} + 35.2°$ (c=1, $H_2O$).
TLC: Rf=0.61.

EXAMPLE 30

N-(4-bromobenzyl)valiolamine

In 50 ml of methanol is dissolved 900 mg of valiolamine, and to the solution are added 40 ml of dioxane, 1.6 g of sodium hydrogencarbonate and 3.0 g of p-bromobenzyl bromide, followed by stirring at room temperature for 20 hours. The reaction solution is filtered, and the insoluble materials are washed with methanol. The filtrate and washings are combined and concentrated under reduced pressure, and ethyl acetate and water are added to the residue. The mixture, while stirring, is adjusted to pH 2 with 2N hydrochloric acid, and the water layer is separated, washed with water and concentrated under reduced pressure. The concentrate is chromatographed on a column (300 ml) of MCI Gel CHP20P (produced by Mitsubishi Chemical Ind., Ltd.), and after the column is washed with water, the elution is accomplished with a water-methanol gradient. The eluate are combined, and the methanol is distilled off under reduced pressure. The concentrate is adjusted to pH 10, whereby crystals separate out. Yield of 750 mg. Recrystallization from ethanol gives N-(4-bromobenzyl)valiolamine in crystals.

Melting point of 206° to 208° (decomp.).

Elemental analysis, for $C_{14}H_{20}NO_5Br$: Calcd.(%): C, 46.42; H, 5.57; N, 3.87; Br, 22.06; Found (%): C, 46.39; H, 5.49; N, 3.86; Br, 22.23.

$[\alpha]_D^{24} + 3.9°$ (c=1, MeOH).
TLC: Rf=0.63.

N-(p-bromobenzyl)valiolamine has been confirmed to be the following structural formula by X-ray crystallographical analysis.

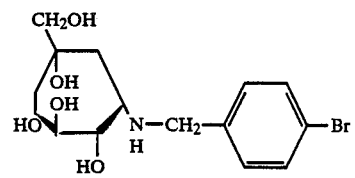

EXAMPLE 31

N-(3-phenylallyl)valiolamine

In 20 ml of methanol is dissolved 1.0 g of valiolamine, and 1.3 ml of cinnamaldehyde is added to the solution, followed by stirring at room temperature for 2 hours. The precipitated Schiff's base is recovered by filtration and dried under reduced pressure. 1.5 g of the Schiff's base is suspended in 20 ml of methanol, and 210 mg of sodium borohydride is added to the suspension under ice-cooling, followed by stirring at the same temperature for 2 hours. To the reaction solution are added water, acetone and n-butyl alcohol, and the mixture is concentrated under reduced pressure to distill off the organic solvent. The aqueous solution is adjusted to pH 2 and washed with ethyl acetate. The water layer is further concentrated under reduced pressure to about 20 ml. The concentrate is chromatographed on a column (250 ml) of MCI Gel CHP20P (produced by Mitsubishi Chemical Ind., Ltd.), and after the column is washed with water, the elution is accomplished with a water-methanol gradient. The eluate is concentrated under reduced pressure and lyophilized to give N-(3-phenylallyl)valiolamine hydrochloride. Yield of 1.3 g.

Elemental analysis, for $C_{16}H_{23}NO_5.HCl.\frac{1}{2}H_2O$: Calcd.(%): C, 54.16; H, 7.10; N, 3.95; Cl, 9.99; Found (%): C, 54.22; H, 7.14; N, 4.04; Cl, 10.45.

$[\alpha]_D^{26} + 36.0°$ (c=1, $H_2O$).
TLC: Rf=0.66.

EXAMPLE 32

N-furfurylvaliolamine

In 15 ml of methanol is dissolved 1.0 g of valiolamine, and 1 ml of 2-furaldehyde is added to the solution, followed by stirring at room temperature for 2.5 hours. The reaction solution is concentrated under reduced pressure, and ethyl ether is added to the residue. The resultant precipitates are recovered by filtration and dried. 1.33 g of the Schiff's base thus obtained is suspended in 15 ml of methanol, and 200 mg of sodium borohydride is added to the suspension under ice-cooling, followed by stirring at the same temperature for 2 hours. To the reaction solution are added water, acetone and n-butyl alcohol, and the mixture is concentrated under reduced pressure to distill off the organic solvent. The resultant aqueous solution is chromatographed on a column (180 ml) of MCI Gel CHP20P (produced by Mitsubishi Chemical Ind., Ltd.), and after the column is washed with water, the elution is accomplished with a water—60% aqueous methanol gradient. The eluate is concentrated under reduced pressure and then lyophilized to give 1.1 g of N-furfurylvaliolamine.

Elemental analysis, for $C_{12}H_{19}NO_6$: Calcd.(%): C, 52.74; H, 7.01; N, 5.13; Found (%): C, 52.68; H, 7.25; N, 5.38.

$[\alpha]_D^{26} +20.1°$ (c=1, $H_2O$).
TLC: Rf=0.48.

EXAMPLE 33

N-thenylvaliolamine

In 20 ml of methanol is dissolved 1.0 g of valiolamine, and 1.0 ml of thiophenecabaldehyde, followed by stirring at room temperature for 1 hour. The reaction mixture is concentrated, and ethyl ether is added to the residue. The resultant precipitates are recovered by filtration and dried. 1.35 g of the Schiff's base thus obtained is suspended in 50 ml of methanol, and 210 mg of sodium borohydride is added to the suspension under ice-cooling, followed by stirring at room temperature for 4 hours. To the reaction solution are added water, acetone and n-butyl alcohol, and the mixture is concentrated under reduced pressure to distill off the organic solvent. The concentrate is chromatographed on a column of 180 ml of MCI Gel CHP20P (produced by Mitsubishi Chemical Ind., Ltd.), and after the column is washed with water, the elution is accomplished with a water-methanol gradient. The eluate is concentrated under reduced pressure, whereby crystals of N-thenyl-valiolamine separate out. Yield of 500 mg. Further, 550 mg of N-thenylvaliolamine is recovered from the mother liquor.

Elemental analysis, for $C_{12}H_{19}NO_5S$: Calcd.(%): C, 49.81; H, 6.62; N, 4.84; S, 11.08; Found (%): C, 49.87; H, 6.59; N, 4.81; S, 11.06.

$[\alpha]_D^{26} +25.6°$ (c=1, $H_2O$).
TLC: Rf=0.54.

EXAMPLE 34

N-(3-pyridylmethyl)valiolamine

In 10 ml of methanol is dissolved 1.0 g of valiolamine, and 0.6 ml of nicotinaldehyde is added to the solution, followed by stirring at room temperature for 1 hour. The reaction solution is concentrated under reduced pressure, and ethyl ether is added to the residue to give a precipitate. The supernatant is removed, and the precipitates are dried. 50 ml of methanol is added to 1.5 g of the Schiff's base thus obtained, and 270 mg of sodium borohydride is added to the mixture under ice-cooling, followed by stirring at the same temperature for 1 hour. Further, 5 ml of water is added to the reaction mixture, which is stirred at room temperature for 1 hour. To the reaction solution are added water, acetone and n-butyl alcohol, and the mixture is concentrated under reduced pressure to distill off the organic solvent. The resultant aqueous solution is chromatographed on a column (250 ml) of MCI Gel CHP20P (produced by Mitsubishi Chemical Ind., Ltd.), and after the column is washed with water, the elution is accomplished with a water—60% aqueous methanol gradient. The eluate is concentrated under reduced pressure, and the concentrate is chromatographed on a column (250 ml) of Dowex 1×2 (OH⁻ type) (produced by Dow Chemical Co.), followed by the elution with water. The eluate is concentrated under reduced pressure and lyophilized to give N-(3-pyridylmethyl)valiolamine. Yield of 0.6 g.

Elemental analysis, for $C_{13}H_{20}N_2O_5 \cdot H_2O$: Calcd.(%): C, 51.64; H, 7.34; N, 9.27; Found (%): C, 51.91; H, 7.42; N, 8.92.

$[\alpha]_D^{26} +9.2°$ (c=1, $H_2O$).
TLC: Rf=0.13.

EXAMPLE 35

N-(2-hydroxy-3-phenoxypropyl)valiolamine 4.7 g of phenol is dissolved in aqueous solution of 2.2 g of sodium hydroxide (10 ml) under a stream of nitrogen, and 5 g of epichlorohydrin is added to the solution, followed by stirring at room temperature for 24 hours. 50 ml of water is added to the reaction solution, and the mixture is extracted with two portions of 50 ml of dichloromethane. The dichloromethane layer is washed with water, dried over sodium sulfate and freed of the solvent to give 7 g of a mixture of 1-phenoxy-2,3-epoxypropane and 1-chloro-2-hydroxy-3-phenoxypropane.

5.8 g of sodium hydrogen carbonate is added to a solution of 2.0 g of valiolamine in 55 ml of N,N-dimethylformamide, followed by adding 7 g of the above mixture of 1-phenoxy-2,3-epoxypropane and 1-chloro-2-hydroxy-3-phenoxypropane. The mixture is stirred for 5 hours while the bath temperature is maintained at 90° C. The reaction solution is filtered, and the filtrate is concentrated under reduced pressure to distill off the solvent. Water and n-butyl alcohol are added to the residue. The mixture is adjusted to pH 2 with 2N hydrochloric acid, and the residue is partitioned between n-butyl alcohol and water. The n-butyl alcohol layer is extracted with water. The water layers are combined and concentrated under reduced pressure. The concentrate is chromatographed on a column of MCI Gel CHP20P (250 ml) (produced by Mitsubishi Chemical Ind., Ltd.), and the elution is conducted with water. The eluate is concentrated under reduced pressure and lyophilized to give 540 mg of white powder of N-(2-hydroxy-3-phenoxypropyl)valiolamine hydrochloride.

Elemental analysis, for $C_{16}H_{25}NO_7 \cdot HCl \cdot \frac{1}{2}H_2O$: Calcd.(%): C, 49.42; H, 7.00; N, 3.60; Cl, 9.12; Found (%): C, 49.11; H, 7.45; N, 3.79; Cl, 9.59.

$[\alpha]_D^{24} +15.3°$ (c=1, $H_2O$)
TLC: Rf=0.60.

EXAMPLE 36

N-(2-hydroxycyclohexyl)valiolamine

In 100 ml of methanol are dissolved 2.0 g of valiolamine and 2 ml of 1,2-epoxycyclohexane, and the solution is heated under reflux with stirring. After the reaction was continued for 5 hours, 4 ml of 1,2-epoxycyclohexane is further added, and the reaction mixture is furthermore heated under reflux with stirring for 10 hours. The reaction solution is concentrated under reduced pressure, and ethyl ether is added to the residue, followed by recovering by filtration the resultant precipitates. The obtained powder is dissolved in a small amount of water and chromatographed on a column of Amberlite CG-50 (NH$_4$+ type, 400 ml, produced by Rohm & Haas Co., U.S.A.), and elution with water allows separation into two components. The first eluted fractions (each 19 g, fraction Nos. 38-80) are combined, concentrated under reduced pressure and lyophilized to give an optical isomer (yield of 1.1 g) of N-(2-hydroxycyclohexyl)valiolamine showing $[\alpha]_D^{24}$ −41.9° (c=1, H$_2$O). On the other hand, the subsequently eluted fractions (each 19 g, fraction No. 91-297) are combined, concentrated under reduced pressure and lyophilized to give another optical isomer (yield of 0.95 g) of N-(2-hydroxycyclohexyl)valiolamine showing $[\alpha]_D^{24}$ +43.4° (c=1, H$_2$O). Isomer showing $[\alpha]_D^{24}$ −41.9°:

Elemental analysis, for C$_{13}$H$_{25}$NO$_6$·½H$_2$O: Calcd.(%): C, 52.77; H, 8.69; N, 4.73; Found (%): C, 52.72; H, 8.89; N, 4.72.

TLC: Rf=0.51.

IC$_{50}$(maltase): 6.1×10$^{-9}$M.

IC$_{50}$(saccharase): 5.2×10$^{-9}$M.

Isomer showing $[\alpha]_D^{24}$ +43.4°:

Elemental analysis, for C$_{13}$H$_{25}$NO$_6$·½H$_2$O: Calcd.(%): C, 51.98; H, 8.73; N, 4.66; Found (%): C, 51.76; H, 9.11; N, 4.81.

TLC: Rf=0.48.

IC$_{50}$(saccharase): 1.6×10$^{-7}$M.

EXAMPLE 37

N-cyclohexylvaliolamine

In 50 ml of dimethylformamide are dissolved 2.0 g of valiolamine and 3.5 ml of cyclohexane, and 1.5 ml of 2N hydrochloric acid and 2.6 g of sodium cyanoborohydride are added to the solution, followed by stirring at 60° to 70° C. for 17 hours. The reaction solution is concentrated under reduced pressure, and the residue is dissolved in about 100 ml of water. 200 ml of Dowex 50W×8 (H+ type, produced by Dow Chemical Co. U.S.A.) are added to the solution, and the mixture is stirred for about 1 hour and poured on a column of Dowex 50W×8 (H+ type, 100 ml). After the column is washed with water, elution is conducted with 0.5N aqueous ammonia. The eluate (1.2 to 3.5 l) is concentrated under reduced pressure, and the resultant concentrate (about 20 ml) is chromatographed on a column of Amberlite (NH$_4$+ type, produced by Rohm & Haas Co., 250 ml), followed by elution with water. The eluate (700 ml to 6.8 l) is concentrated under reduced pressure and lyophilized to give 1.4 g of N-cyclohexylvaliolamine.

$[\alpha]_D^{24}$ +10.8° (c=1, H$_2$O).

Elemental analysis, for C$_{13}$H$_{25}$NO$_5$·½H$_2$O: Calcd.(%): C, 54.91; H, 9.22; N, 4.93; Found (%): C, 55.13; H, 9.23; N, 4.94.

TLC: Rf=0.56.

IC$_{50}$(maltase): 4.1×10$^{-7}$M.

IC$_{50}$(saccharase): 1.5×10$^{-8}$M.

EXAMPLE 38

N-(2-hydroxycyclopentyl)valiolamine

In 100 ml of methanol is dissolved 2.0 g of valiolamine, and 6.0 ml of 1,2-epoxycyclopentane is added, followed by heating under reflux for 24 hours. The reaction solution is concentrated under reduced pressure, and ethyl ether is added to the residue, whereby precipitates result. The supernatant solution is removed by decantation, and the precipitates are dissolved in water (about 100 ml). The solution is concentrated under reduced pressure to about 20 ml, and the concentrate is chromatographed on a column of Amberlite CG-50 (NH$_4$+ type, produced by Rohm & Haas Co., 400 ml). Elution with water allows separation into the first eluate (fraction containing a component with Rf=0.48; fraction Nos. 24 through 28, each 19 g) and the subsequent eluate (fraction containing a component mainly with Rf=0.43; fraction Nos. 29 through 70, with each fraction weighing 19 ). The subsequently eluted fractions (fraction Nos. 29 through 70) is concentrated under reduced pressure to about 40 ml and chromatographed on a column of Amberlite CG-50 (NH$_4$+ type, 500 ml), and elution with water (each fraction weighing 19 g) permits separation into an eluate containing a component with Rf=0.48 (fraction Nos. 36 to 40), an eluate containing components having Rf=0.48 and 0.43, respectively, (fraction Nos. 41 to 50) and an eluate containing a component with Rf=0.43 (fraction Nos. 51 through 70). The eluate consisting of fraction Nos. 41 through 50 is once again chromatographed on a column of Amberlite CG-50 (NH$_4$+ type, 270 m), and separated into an eluate containing a component with Rf=0.48 (fraction Nos. 21 to 23) and an eluate containing a component with Rf=0.43 (fraction Nos. 27 through 44) by elution with water (each fraction weighing 19 g). The eluates containing a component with Rf=0.48 are combined, concentrated under reduced pressure and lyophilized to give an optical isomer (yield of 0.5 g) of N-(2-hydroxycyclopentyl)valiolamine showing $[\alpha]_D^{24}$ −16.2° (c=1, H$_2$O). On the other hand, the eluates containing a component with Rf=0.43 are combined, concentrated under reduced pressure and lyophilized to give another optical isomer (yield of 0.4 g) of N-(2-hydroxycyclopentyl)valiolamine showing $[\alpha]_D^{24}$ +40.4° (c=1.0).

Isomer showing $[\alpha]_D^{24}$ −16.2° (c=1, H$_2$O):

Elemental analysis, for C$_{12}$H$_{23}$NO$_6$·½H$_2$O: Calcd.(%): C, 50.34; H, 8.45; N, 4.89; Found (%): C, 50.73; H, 8.40; N, 4.86.

TLC: Rf=0.48.

IC$_{50}$(maltase): 5.8×10$^{-8}$M.

IC$_{50}$(saccharase): 2.4×10$^{-8}$M.

Isomer showing $[\alpha]_D^{24}$ +40.4° (c=1, H$_2$O):

Elemental analysis, for C$_{12}$H$_{23}$NO$_6$·½H$_2$O: Calcd.(%): C, 50.34; H, 8.45; N, 4.89; Found (%): C, 50.43; N, 8.93; N, 4.87.

TLC: Rf=0.43.

IC$_{50}$(saccharase): 1.3×10$^{-7}$M.

EXAMPLE 39

N-cyclopentylvaliolamine

In 50 ml of dimethylformamide are dissolved 2.0 g of valiolamine and 3.5 ml of cyclopentanone, and 1.5 ml of 2N hydrochloric acid and 2.6 g of sodium cyanoborohydride are added to the solution, followed by stirring at 60° to 70° C. for 18 hours. The reaction solution is concentrated under reduced pressure to distill off the dimethylformamide, and toluene is further added to the residue, followed by repeating concentration under reduced pressure. The residue is dissolved in 50 ml of water, and 200 ml of Dowex 50W×8 (H+ type, produced by Dow Chemical Co.) is added to the solution, followed by stirring for 1 hour. The mixture is poured on a column packed with 100 ml of Dowex 50W×8 (H+ type), and after the column is washed with water (1.8 l), elution is conducted with 0.5N aqueous ammonia. The eluate (fractions of 1.45 to 2.2 l) is concentrated under reduced pressure, and the concentrate is chromatographed on a column of Amberlite CG-50 (NH$_4^+$ type, produced by Rohm & Haas, Co., 250 ml), followed by elution with water. The eluate (fractions of 520 ml to 2.8 l) is concentrated under reduced pressure and lyophilized to give 1.2 g of white powder of N-cyclopentylvaliolamine.

$[\alpha]_D^{23}$ +8.0° (c=1, H$_2$O).

Elemental analysis, for C$_{12}$H$_{23}$NO$_5$: Calcd.(%): C, 55.15; H, 8.87; N, 5.36; Found (%): C, 55.27; H, 8.99; N, 5.62.

TLC: Rf=0.50.

IC$_{50}$(saccharase): 2.5×10$^{-8}$M.

EXAMPLE 40

N-(3,5-di-tert-butyl-4-hydroxybenzyl)valiolamine

A 3.0 g portion of valiolamine and 7.0 g of 3,5-di-tert-butyl-4-hydroxybenzaldehyde are stirred in 30 ml of methanol at 40° C. for 2 hours. The reaction solution is concentrated under reduced pressure, and petroleum ether is added to the residue, followed by recovering by filtration the resultant precipitates. The obtained Schiff's base is dissolved in 50 ml of methanol, and 1.0 g of sodium borohydride is added little by little to the solution under ice-cooling, followed by stirring further for 2.5 hours. The reaction solution is concentrated under reduced pressure, and to the residue are added ethylacetate and water. After the mixture is adjusted to pH 2 with 2N hydrochloric acid under stirring, the water layer is separated and washed with ethyl acetate. Ethyl acetate is added to the water layer and the mixture is adjusted to pH 10 with N-sodium hydroxide under stirring to separate the ethyl acetate layer. The ethyl acetate layer is washed with water, dried over anhydrous magnesium sulfate and concentrated under reduced pressure. Petroleum ether is added to the residue, and when the mixture is allowed to stand overnight, to give 3.0 g of N-(3,5-di-tert-butyl-4-hydroxybenzyl)valiolamine.

Elemental analysis, for C$_{22}$H$_{37}$NO$_6$: Calcd.(%): C, 64.21; H, 9.06; N, 3.40; Found (%): C, 64.00; H, 9.34; N, 3.25.

$[\alpha]_D^{24}$ −2.3° (c=1, CH$_3$OH).

TLC: Rf=0.80.

IC$_{50}$(maltase): 4.3×10$^{-8}$M.

IC$_{50}$(saccharase): 6.8×10$^{-9}$M.

EXAMPLE 41

N-(β-hydroxy-2-methoxyphenetyl)valiolamine

In a mixed solution of 20 ml of dimethylformamide and 100 ml of methanol are dissolved 4.1 g of valiolamine and 4.0 g of 2-methoxyphenylglyoxal, and the solution is stirred at room temperature for 1.5 hours, 1.2 g of sodium borohydride is added to the solution under cooling with ice-cold water, and the mixture is stirred at room temperature for 1 hour. The reaction solution is concentrated under reduced pressure, and ethyl acetate and water are added to the residue, and the mixture is adjusted to pH 2 with 2N hydrochloric acid under stirring. The water layer is separated and the ethyl acetate layer is extracted with 1/10N hydrochloric acid. The water layers are combined, adjusted to pH 10 with N sodium hydroxide and concentrated under reduced pressure. The concentrate is chromatographed on a column of Dowex 50W×8 (H$^+$ type, 400 ml, produced by Dow Chemical Co.). After the column is washed with water, elution is accomplished with 0.5N aqueous ammonia. The eluate is concentrated under reduced pressure, and the residue is chromatographed on a column of MCI Gel CHP20P (250 ml, produced by Mitsubishi Chemical Ind.). After the column is washed with water, elution is conducted with a water (1 l)-methanol(1 l) gradient. The eluate is concentrated under reduced pressure and the residue is lyophilized to give 3.0 g of white powder of N-(β-hydroxy-2-methoxyphentyl)valiolamine.

Elemental analysis, for C$_{16}$H$_{25}$NO$_7$.½H$_2$O: Calcd.(%): C, 54.53; H, 7.44; N, 3.98; Found (%): C, 54.36; H, 7.35; N, 3.86.

$[\alpha]_D^{24}$ +11.9° (c=1, H$_2$O).

TLC: Rf=0.63.

IC$_{50}$(maltase): 6.3×10$^{-8}$M.

IC$_{50}$(saccharase): 9.9×10$^{-9}$M.

EXAMPLE 42

To 200 ml of a beverage admixed with fruit juice is added 100 mg of N-(1,3-dihydroxy-2-propyl)validamine, and the mixture is stirred to make a solution.

EXAMPLE 43

N-(β-hydroxyphenetyl)validamine hydrochloride:
20 parts by weight
Lactose:
100 parts by weight The above two are uniformly mixed and processed into a form of powder or fine granule to produce a powder preparation.

EXAMPLE 44

After the production steps for strawberry jam (cooking and heating treatment) in accordance with the conventional method is completed, when the temperature of the product decreases to 50° C., N-(2-hydroxycyclopentyl)validamine is uniformly blended into it at a ratio of 0.4% relative to the weight of the finished product, followed by cooling to obtain the strawberry jam.

EXAMPLE 45

In accordance with the conventional method, 7 kg of sugar is added to 10 kg of strawberry fruit, and the mixture is boiled with stirring until it jells. When the temperature of the product decreases to about 50° C., N-(β-hydroxyphenetyl)valiolamine is uniformly blended into it at a ratio of 0.5% relative to the weight of the finished product, followed by cooling to obtain the strawberry jam product.

EXAMPLE 46

To 200 ml of a beverage admixed with fruit juice is added 100 mg of N-(1,3-dihydroxy-2-propyl)valiolamine, followed by stirring to make a uniform solution.

EXAMPLE 47

N-phenetylvaliolamine hydrochloride:
20 parts by weight
Lactose:
80 parts by weight
Crystalline cellulose:
20 parts by weight The above three are mixed and kneaded with water. The mixture is processed into a form of powder or fine granule to produce a powder preparation.

EXAMPLE 48

To 200 ml of a beverage admixed with fruit juice is added 30 mg of N-cyclohexylvaliolamine, followed by stirring to make a uniform mixture.

EXAMPLE 49

N-(2-hydroxycyclohexyl)valiolamine:
10 parts by weight
Lactose:
100 parts by weight The above two are uniformly mixed, and the mixture is processed into a form of powder or fine granules to produce a powder preparation.

What is claimed is:

1. A compound of the formula:

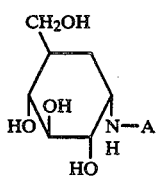

wherein A is a chain hydrocarbon group having 1 to 10 carbon atoms which may be substituted by
  hydroxyl,
  phenoxy,
  thienyl,
  furyl,
  pyridyl,
  phenyl which may be substituted by hydroxyl, lower alkoxy, lower alkyl or halogen,
  or a cyclic hydrocarbon group having 3 to 7 carbon atoms which may be substituted by hydroxyl.

2. A compound as claimed in claim 1 wherein A is a chain hydrocarbon of 1 to 6 carbon atoms which may be substituted by hydroxyl.

3. A compound as claimed in claim 1 wherein A is chain hydrocarbon of 1 to 6 carbon atoms which may be substituted by a phenyl which may be substituted by hydroxyl, lower alkoxy, lower alkyl or halogen.

4. A compound as claimed in claim 1 wherein A is a chain hydrocarbon having 1 to 10 carbon atoms which may be substituted by cyclohexyl or hydroxycyclohexyl.

5. A compound as claimed in claim 1, namely N-(1,3-dihydroxy-2-propyl)validamine.

6. A compound as claimed in claim 1, namely N-($\beta$-hydroxyphenethyl)validamine.

* * * * *